US012710409B1

(12) United States Patent
Nallon

(10) Patent No.: US 12,710,409 B1
(45) Date of Patent: Aug. 18, 2026

(54) TRAINING SYSTEM AND APPARATUS FOR ARTIFICIAL OLFACTION USING CHEMICAL SENSOR ARRAYS

(71) Applicant: Black Cow Labs, LLC, Earlysville, VA (US)

(72) Inventor: Eric Nallon, Earlysville, VA (US)

(73) Assignee: Black Cow Labs, LLC, Earlysville, VA (US)

( * ) Notice: Subject to any disclaimer, the term of this patent is extended or adjusted under 35 U.S.C. 154(b) by 0 days.

(21) Appl. No.: 19/353,872

(22) Filed: Oct. 9, 2025

(51) Int. Cl.
*G01N 33/00* (2006.01)

(52) U.S. Cl.
CPC ..... *G01N 33/0001* (2013.01); *G01N 33/0011* (2013.01); *G01N 33/0073* (2013.01)

(58) Field of Classification Search
None
See application file for complete search history.

(56) References Cited

U.S. PATENT DOCUMENTS

| | | | |
|---|---|---|---|
| 6,744,488 B2 | 6/2004 | Schermerhorn | |
| 6,783,084 B1 | 8/2004 | Nelson | |
| 8,930,341 B2 | 1/2015 | Amin et al. | |
| 9,517,286 B1 * | 12/2016 | Li | A61L 9/145 |
| 9,645,127 B2 | 5/2017 | Amin et al. | |
| 10,688,389 B2 | 6/2020 | Flego et al. | |
| 11,409,797 B2 | 8/2022 | Su et al. | |
| 11,583,604 B1 | 2/2023 | Gressick et al. | |
| 11,890,535 B2 | 2/2024 | Flego et al. | |
| 11,975,491 B2 | 5/2024 | Ivanov et al. | |
| 12,005,649 B2 | 6/2024 | Ivanov et al. | |

(Continued)

FOREIGN PATENT DOCUMENTS

| | | |
|---|---|---|
| CN | 110252079 B | 3/2022 |
| WO | 1999016476 A1 | 4/1999 |

(Continued)

OTHER PUBLICATIONS

T Maekawa, Kuiqian Cai, K Suzuki, N Dougami, T Takada, M Egashira, Compensatory methods for the odor concentration in an electronic nose system using software and hardware, Sensors and Actuators B: Chemical, vol. 76, Issues 1-3, 2001, pp. 430-435, ISSN 0925-4005 (Year: 2001).*

(Continued)

*Primary Examiner* — Lina Cordero
(74) *Attorney, Agent, or Firm* — Leech Tishman Fuscaldo & Lampi, LLC

(57) ABSTRACT

A computer-implemented olfactory data processing system includes a system controller programmed for selecting at least one vial containing a predetermined compound; activating a relay to transmit the predetermined compound in the selected vial to a mixing manifold; and directing at least one mass flow controller (MFC) for processing a sample of the predetermined compound. The mixing manifold can be configured for processing the predetermined compound to produce a target vapor as a test sample for analysis. A sensor is configured for sensing at least one olfactory attribute of the test sample. Also, a data acquisition module operatively associated with the system controller can be programmed for receiving signals communicated from the sensor indicative of sensor data.

20 Claims, 21 Drawing Sheets

(56) References Cited

U.S. PATENT DOCUMENTS

| | | | | |
|---|---|---|---|---|
| 2004/0101447 | A1* | 5/2004 | Tajima | A61L 9/125 422/123 |
| 2009/0104072 | A1* | 4/2009 | Ando | A61L 9/04 422/123 |
| 2010/0131206 | A1* | 5/2010 | Angell | G06Q 30/02 702/23 |
| 2016/0091470 | A1* | 3/2016 | Gafsou | G01N 33/0034 73/23.34 |
| 2019/0160195 | A1* | 5/2019 | Kelsen | A61L 9/125 |
| 2020/0183925 | A1 | 6/2020 | Amin et al. | |
| 2020/0289694 | A1* | 9/2020 | Kelsen | A61L 9/122 |
| 2020/0324011 | A1* | 10/2020 | Jin | A61L 9/035 |
| 2021/0213237 | A1* | 7/2021 | Kelsen | B60H 1/00742 |
| 2022/0091571 | A1 | 3/2022 | Ivanov et al. | |
| 2022/0406417 | A1 | 12/2022 | Kaneko et al. | |
| 2023/0032568 | A1* | 2/2023 | Arkhipov | G01N 21/554 |
| 2024/0000368 | A1* | 1/2024 | Maggioni | A61B 5/4011 |
| 2024/0170107 | A1 | 5/2024 | Silver et al. | |
| 2024/0272703 | A1 | 8/2024 | Vemparala Guruswamy et al. | |
| 2024/0325881 | A1 | 10/2024 | Flego et al. | |
| 2025/0180530 | A1* | 6/2025 | Shido | G08B 3/10 |

FOREIGN PATENT DOCUMENTS

| | | | |
|---|---|---|---|
| WO | 2022085345 | A1 | 4/2022 |
| WO | 2023163028 | A1 | 8/2023 |

OTHER PUBLICATIONS

Wen, Tengteng, et al. "The odor characterizations and reproductions in machine olfactions: a review." Sensors 18.7 (2018): 2329.

St. Croix Sensory, Inc., "Nasal Ranger—Field Olfactometer", https://www.fivesenses.com/equipment/nasalranger.

Wang, Peter Y., et al. "Evolving the olfactory system with machine learning." Neuron 109.23 (2021): 3879-3892.

* cited by examiner

```
# Configuration for compound sampling. All durations are in seconds.
sampler:
  sample_sat_vapor_percent: 25
  baseline_duration: 30
  sample_duration: 20
  recovery_duration: 30
  initial_delay: 3

  compounds:
    repeats: 75
    Vial1:
      compound: Acetone
    Vial2:
      compound: Diesel
    Vial3:
      compound: Hexane
    Vial4:
      compound: Nitrotoluene
    Vial5:
      compound: Formaldehyde
```

Define concentration and sampling times

Define compounds and number of times to repeat

```
# AI/Ml model training and analysis
model_training:
  feature_extraction: True
  preprocess_data: True
  normalize_data: True
  cross_validation: True
  ml_models:
    - random_forest
    - lda
    - knn
    - svm
```

Define ML/AI model training

FIG. 3

```
2024-10-22 20:57:27 INFO    Successfully connected to Sequent DAQ
2024-10-22 20:57:27 INFO    Successfully connected to BME280 Sensor
2024-10-22 20:57:27 INFO    Successfully connected to Sample MFC with input pressure of 14.54psi
2024-10-22 20:57:27 INFO    Successfully connected to Dilution MFC with input pressure of 14.51psi
2024-10-22 20:57:28 INFO    Successfully connected to Redis at localhost:6379
2024-10-22 20:57:28 INFO    Resetting external hardware
2024-10-22 20:57:28 INFO    Setting MFC setpoints to zero
2024-10-22 20:57:28 INFO    Setting Sequent relays: [1, 2, 3, 4, 5, 6, 7, 8] to Low
2024-10-22 20:57:28 INFO    Successfully connected to Redis at localhost:6379
2024-10-22 20:57:28 INFO    Subscribing to channel measurement-progress
```

FIG. 11

| Compound | Average $\Delta R/R_0$ (%) | Standard Deviation |
|---|---|---|
| Acetone | 0.27 | ±0.0391 |
| Acetonitrile | -0.86 | ±0.0508 |
| Chloroform | -1.98 | ±0.0530 |
| Isopropanol | -0.14 | ±0.0267 |
| Methanol | -0.62 | ±0.0370 |
| Toluene | -0.27 | ±0.0170 |

360 Measurements in random order

TRAINING SYSTEM AND APPARATUS FOR ARTIFICIAL OLFACTION USING CHEMICAL SENSOR ARRAYS

FIELD OF THE INVENTION

The present disclosure generally relates to computer-implemented systems, methods, tools, devices, and techniques for processing data associated with odors, smells, and other olfactory attributes of different substances and materials.

BACKGROUND

The olfactory sense is a distinctly human and animal based capability that can be challenging to translate effectively into a computer-based or robotic platform. An effective computer-based olfaction system can provide significant value for existing and emerging applications. For example, there are numerous commercial and non-commercial applications that would benefit from a system which is capable of environmental sensing of volatile organic compounds, toxic industrial chemicals, quality control of composite manufacturing, food and beverage quality control and monitoring, and home-based air quality systems, among many others. An effective machine-based olfaction solution would assist with creating trained detection models, for example, to create labeled training data. There is currently no effective and efficiency solution to create such data based on odors, vapors, and other olfactory related attributes of different substances materials.

Accordingly, a system is needed that is versatile and adaptable to configurable chemical vapor and odor generation, can perform its tasks on an automated or semi-automated basis, and which possesses a sensor-independent or sensor-agnostic interface capable of supporting various types of sensors.

SUMMARY

In various aspects of the present disclosure, a computer-implemented olfactory data processing system is provided which comprises a system controller; and a mixing manifold configured for processing a predetermined compound to produce a target vapor as a test sample. The system controller is programmed for controlling at least one function of multiple components of the system; selecting at least one vial containing a predetermined compound; activating a relay to transmit the predetermined compound in the selected vial to a mixing manifold; and directing at least one mass flow controller (MFC) for processing a sample of the predetermined compound. At least one sensor is provided in the system which is configured for sensing at least one olfactory attribute of the test sample.

BRIEF DESCRIPTION OF THE FIGURES

These and other features and characteristics of the present disclosure, as well as the methods of operation and functions of the related elements of structures and the combination of the parts and economies of manufacture, will become more apparent upon consideration of the following description and the appended claims with reference to the accompanying drawings, all of which form a part of this specification, wherein like reference numerals designate corresponding parts in the various figures.

It is to be expressly understood, however, that the drawings are for the purpose of illustration and description only, and are not intended as a definition of the limit of the disclosure. Further features will become apparent from the following detailed description made with reference to the following drawings:

FIG. 3 includes an example of an input data file an olfactory data processing system structured in accordance with certain aspects of the present disclosure.

FIG. 11 includes an example of a data collection log which can be generated in response to processing performed by an olfactory data processing system structured in accordance with certain aspects of the present disclosure.

DESCRIPTION

In developing the various aspects of the invention described herein, the inventor has appreciated the need for advanced olfaction technology including computer-implemented systems, methods, tools, devices, and techniques for processing data associated with odors, smells, and other olfactory attributes of different substances and materials.

The present disclosure describes a system which is versatile and adaptable to configurable chemical vapor and odor generation, which can perform its tasks on an automated or semi-automated basis, and which possesses a sensor-independent or sensor-agnostic interface capable of supporting various types of sensors.

In various aspects, an olfactory processing system is provided that can be used to perform machine olfaction, digital olfaction, and/or robotic olfaction to perform "smelling" or detection of the olfactory attributes of materials and substances. The olfactory attributes of the materials and substances may be derived from physical, biological or chemical characteristics or other attributes. The system provides the capability to process and analyze a broad range of chemical vapors and odors in a repeatable manner under full automation. The system can collect resulting sensor data derived from exposure to odors or vapors and create a trained models. The interface between the system and the sensor is configured and structured such that the interface is extensible to many different sensor types (e.g., capacitive, resistive, light intensity, colorimetric, and others) and aims to be sensor independent, allowing for integration and interfacing with various sensing modalities into the system.

The system can be used in connection with training machine learning (ML) and/or artificial intelligence (AI) classification and anomaly detection algorithms for use in machine olfaction. A properly trained model (e.g., a digital olfaction model) can provide the ability to artificially smell and also adapt to new odors or olfactory attributes.

Figure 1:
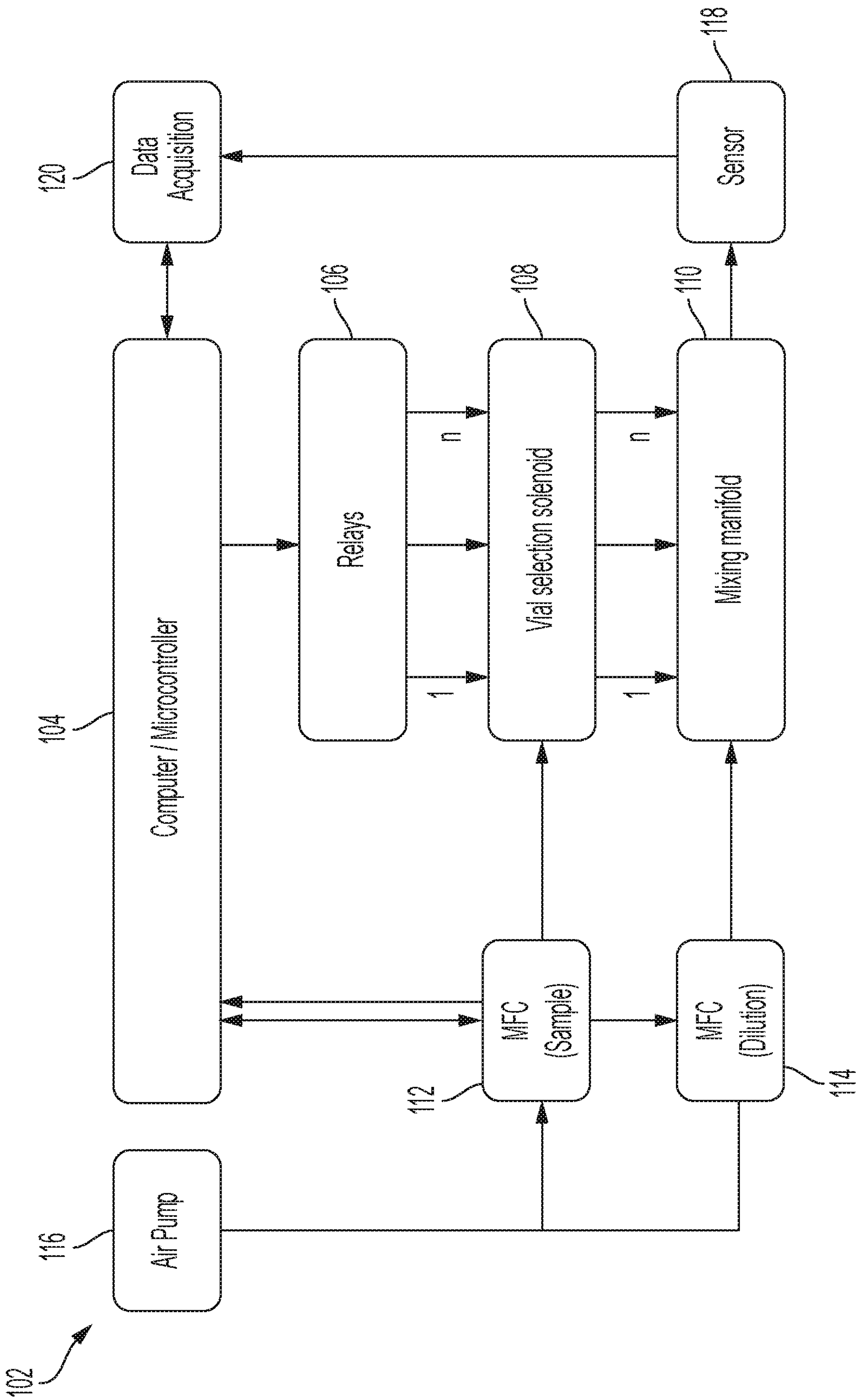
FIG. 1 schematically illustrates one example of an olfactory data processing system structured in accordance with certain aspects of the present disclosure.
Figure 2:
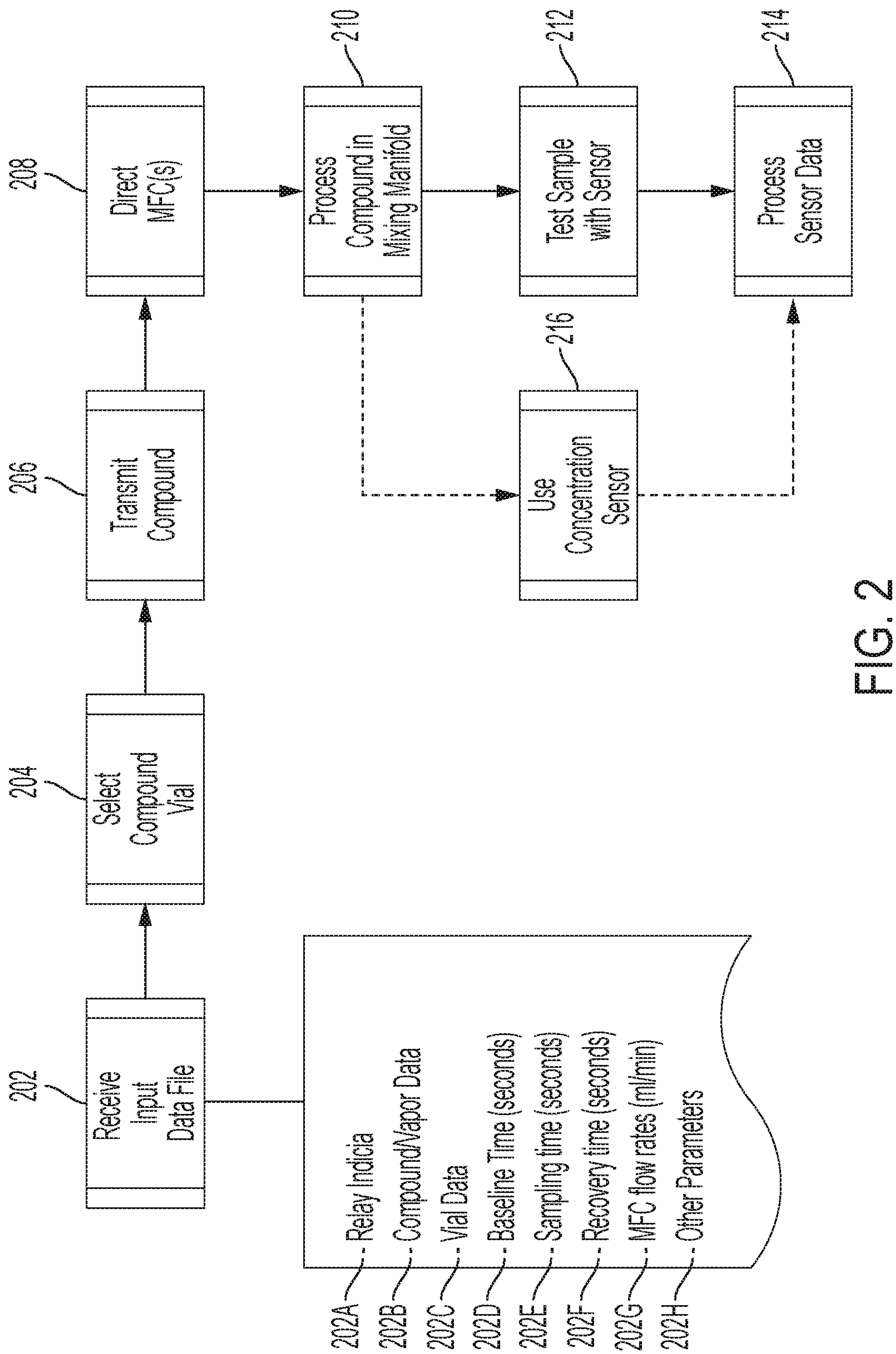
FIG. 2 includes a process flow diagram illustrating examples of processing steps performed by the olfactory data processing system of FIG. 1.
Figure 4:
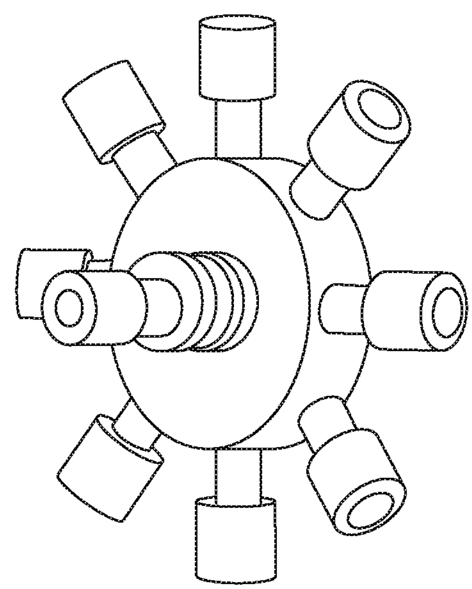
FIGS. 4 through 8 illustrate various examples of manifolds which can be implemented in connection with various aspects of an olfactory data processing system structured in accordance with certain aspects of the present disclosure.
Figure 5:
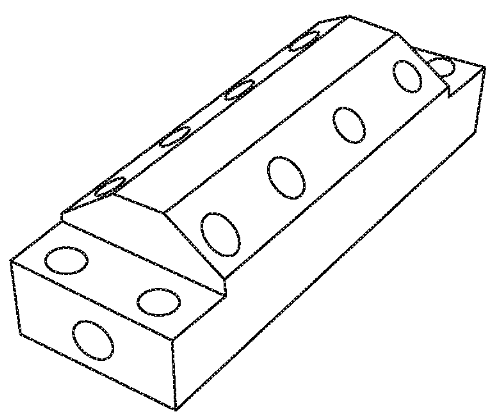
Figure 7:
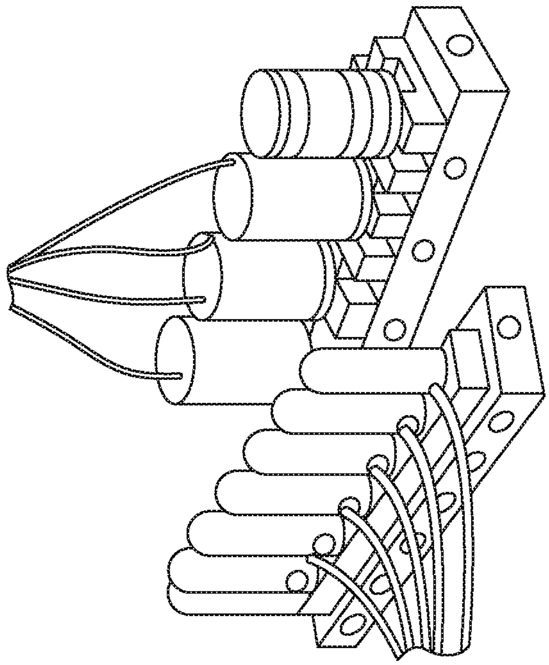
Figure 6:
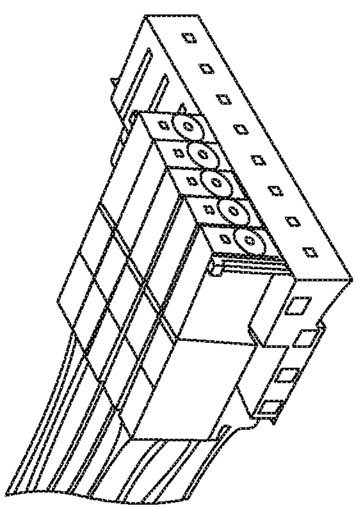
Figure 8:
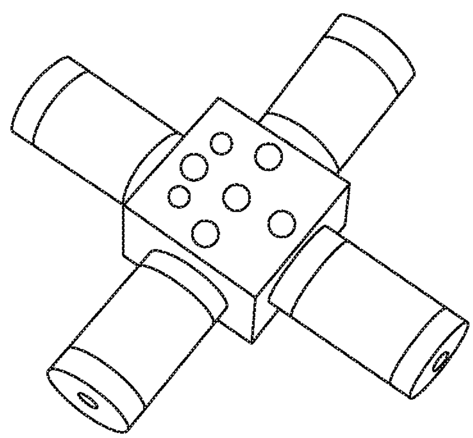

FIGS. 1 and 2 illustrate one example of an olfactory data processing system 102 (see FIG. 1), and the processing steps which can be performed by the system 102 (see FIG. 2), as structured in accordance with various aspects of the present invention. The system 102 can be configured to operate as a vapor delivery system including a system controller 104 programmed with software for controlling and directing the tasks and functions of various components of the system 102. In this example, the controller 104 receives parameter data from an input data file (e.g., a CSV file such as the one shown in FIG. 3) at step 202. The input data file provides various operational and measurement parameters to be used by the controller 104 to assess the composition and attributes of a target vapor. These parameters may include, for example, relay numbers or other relay indicia 202A, compound or vapor data 202B, a specified vial (or vials) data 202C for the particular vial or vials containing the compound, baseline time (seconds) 202D, sampling time (seconds) 202E, recovery time (seconds) 202F, mass flow controller (MFC) flow rates (milliliters/minute) 202G, and/or other parameters 202H. The compound comprising the sample may be in gas, liquid, or solid form.

In other aspects, the system controller 104, in response to the input data received from the input data file, at step 204 can select a vial or vial containing a desired or predetermined compound. At step 206, a relay 106 can be activated in connection with a vial selection solenoid 108 which causes delivery of the compound from the specified vial. The solenoid 108 may also be operatively connected to a web relay 106, for example. Each solenoid 108 may correspond to a single relay 106 and a single bubbler, for example, for transmitting the compound to a mixing manifold 110. Gas delivery from the bubbler to the manifold 110 may be conducted via a one-way check valve comprised of polyetheretherketone (PEEK) material, for example. The web relay 106 may be provided with a built-in, browser-based user interface that makes setup and programming more convenient. The web relay 106 may include software for programming conditional and scheduled logic, such as to control relays, data logging, conducting experiments with the system 102, and other tasks. The web relay 106 can be embodied as a device that combines an electromechanical relay with a built-in web server, allowing for remote control and monitoring of electrical devices over the Internet and/or a local network. Users can interact with the web relay 106 through a web-based browser, making it accessible from various devices and platforms (e.g., a mobile phone, tablet, computer, or other access devices).

In certain aspects, the manifold 110 may comprise a solenoid valve manifold, for example. A solenoid valve manifold is a device that connects multiple solenoid valves together, often in a compact and organized way. These manifolds streamline fluid or gas control by providing a single platform for multiple valves, simplifying plumbing and potentially reducing costs and space. Solenoid valve manifolds can be used to control the flow of liquids and gases in various applications. They can act as a central hub for multiple valves, allowing for the efficient distribution and control of fluids. The manifold 110 can house a number of solenoid valves, each controlling a specific flow path. This allows for complex control sequences and the ability to manage multiple fluid streams from a single unit. The manifold 110 can be structured as a modular design, allowing for customization and flexibility in valve arrangement and configuration. This allows for adapting to the varying needs of different applications and/or experiments. FIGS. 4 through 8 illustrate various examples of manifolds 110 which can be implemented in connection with various aspects of the system 102 described herein.

At step 208, the controller 104 can direct the function of two mass flow controllers (MFCs) 112, 114. Each MFC 112, 114 can be configured to promote accurate and repeatable gas flow measurement and control for the system 102. One MFC 112 can be used for processing a sample of the compound derived from step 206. The other MFC 114 can be configured for diluting or otherwise regulating the concentration of the compound sample processed by the MFC 114. In addition, an air pump 116 can be included in the system 102, for example, to provide positive air flow to the MFCs 112, 114.

At step 210, the compound can be received into and processed by the mixing manifold 110 to produce a target vapor which can be further analyzed by the system 102 as a test sample. In one example, a vapor can be created comprising acetone, methanol, and ether with a baseline time of 30*s*, a sample time of 20*s*, and a recovery time of 60*s*, with a sampling size of 400 times in random order. At step 212, a sensor 118 can be used to test the sample derived from the mixing manifold 110. At step 214, a data acquisition module 120 operatively associated with the system controller 104 can be used to receive signals communicated from the sensor 118 which are indicative of the sensor 118 data. Data collection performed by the system 102 may involve using a web-based application that connects to the system 102 via the web relays 106, for example. In one operation mode, automated data collection can be performed by uploading a predefined Yaml configuration file (as a data input file), for example, and then conducting an experiment.

Figure 9:
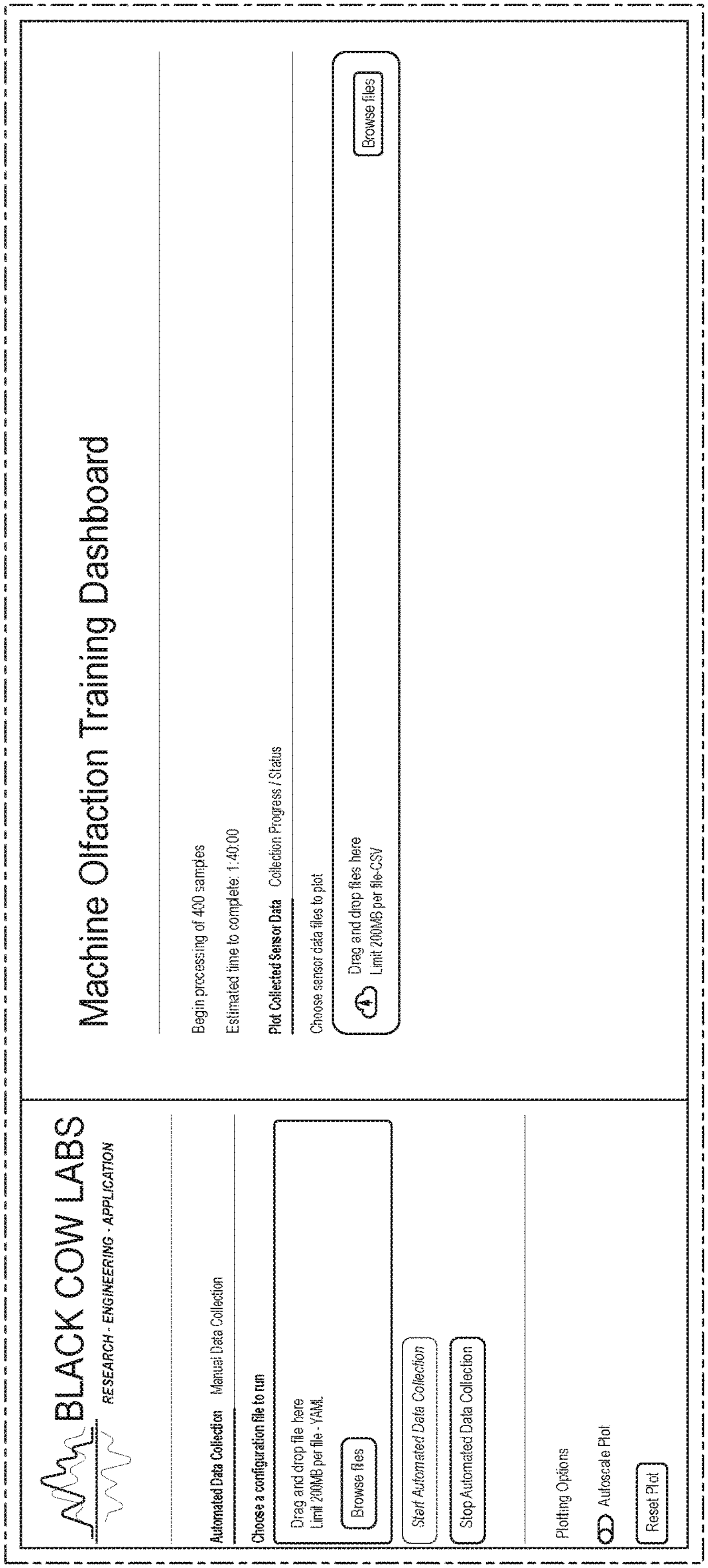
FIGS. 9 and 10 include examples of web-based display screens which can be generated in response to analysis and processing of data by an olfactory data processing system structured in accordance with certain aspects of the present disclosure.
Figure 10:
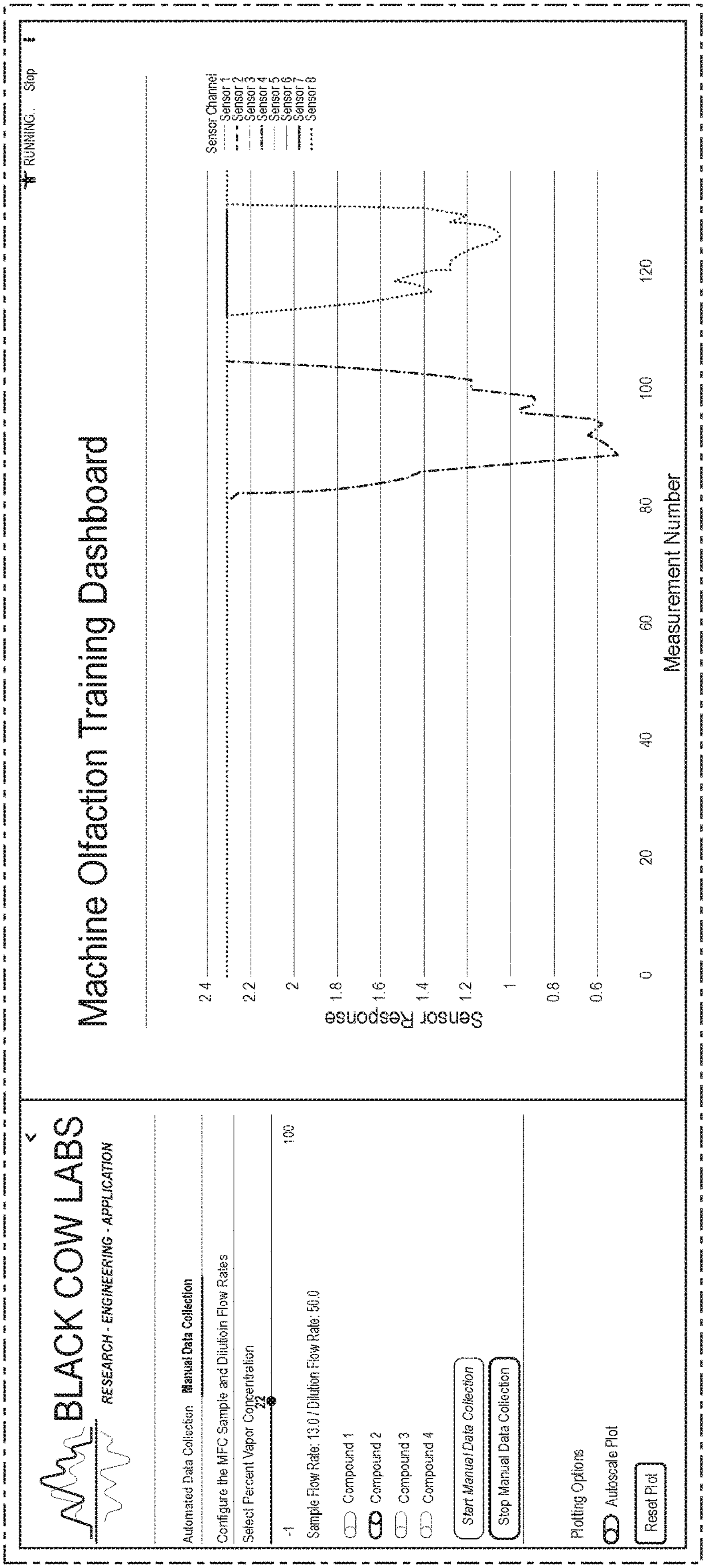

FIGS. 9 and 10 include examples of web-based display screens which can be generated by the system 102 in response to analysis of data acquired from the sensor 118 during an experiment, for example. FIG. 11 includes an example of a data collection log which can be generated in response to the processing performed by the system 102.

Figure 12:
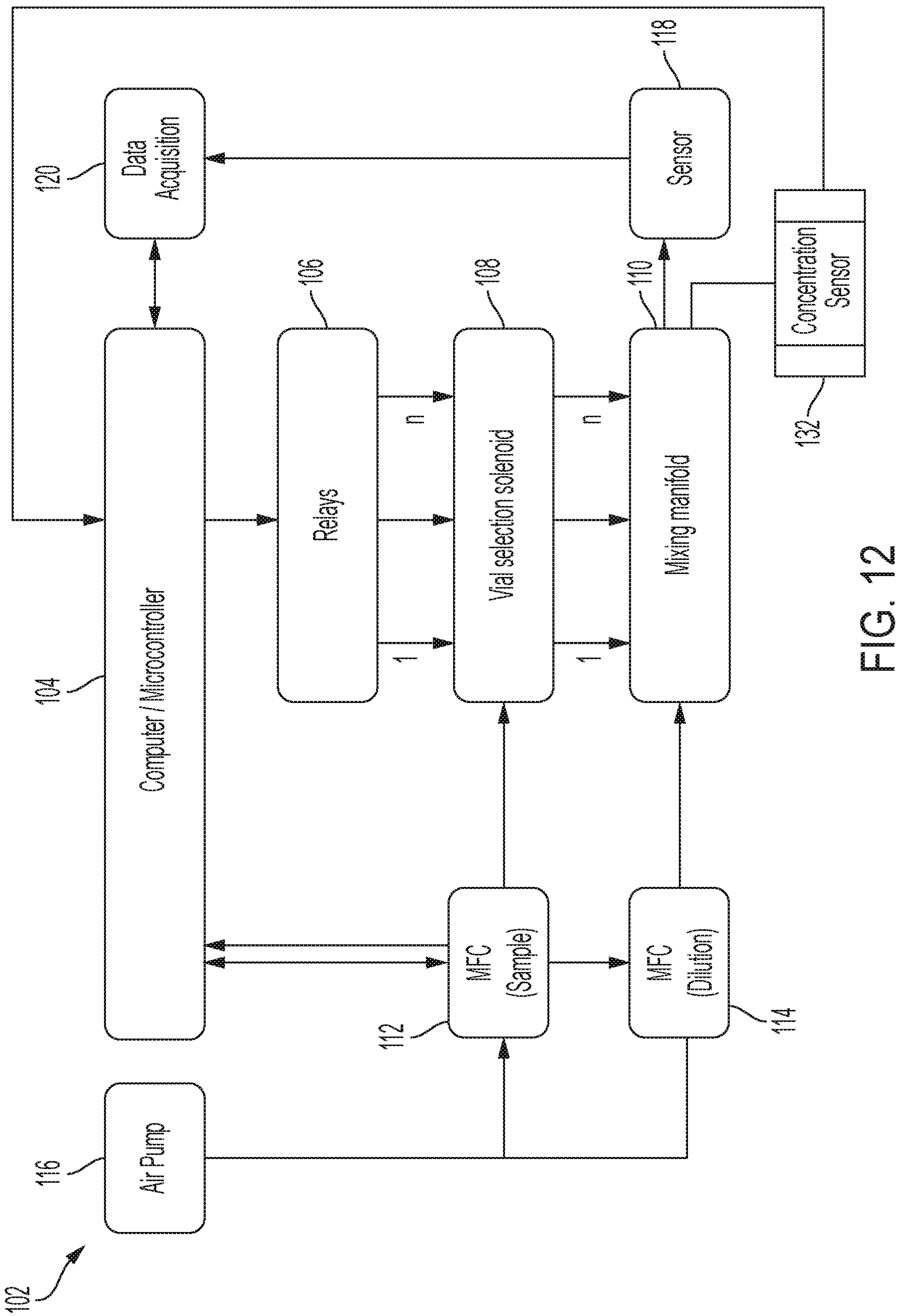
FIG. 12 illustrates an example of an alternative embodiment of the system of FIG. 1 in which a feedback control mechanism can be used for increased system stability.

FIG. 12 illustrates an example of an alternative embodiment of the system 102 in which a feedback control mechanism can be used for increased system 102 stability. At step 216, an optional concentration sensor 132 can be used to measure gas concentration in situ (e.g., at the outlet of the manifold 110) and to communicate feedback concentration data to the system controller 104. The feedback data can be used to dynamically adjust one or more flow rates associated with the MFCs 112, 114, for example, and/or to take other actions within the system 102. Use of the concentration sensor 132 in this manner can allow the system 102 to produce more accurate amounts of target vapor for analysis.

Figure 13:
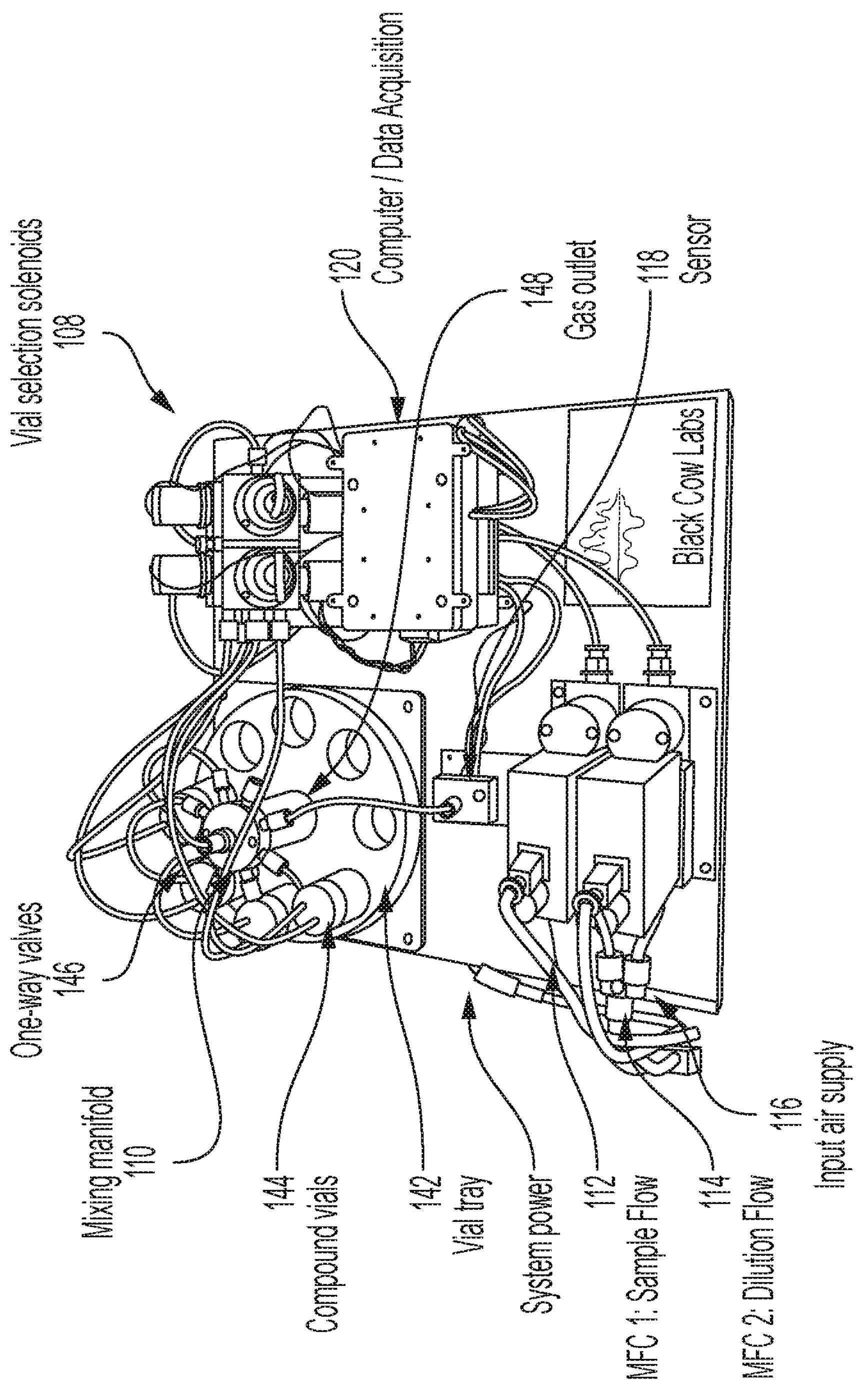
FIG. 13 illustrates a perspective view of another example of the system of FIG. 1.
Figure 14C:
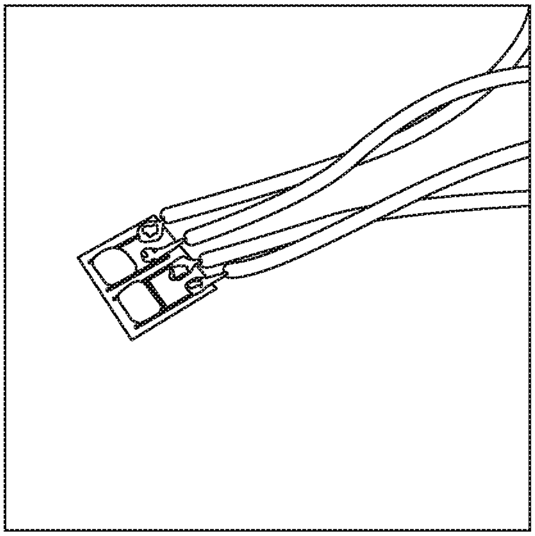
FIGS. 14A-14C include different views of one example of a sensor configured for generating sensor data in response to a test sample.
Figure 14B:
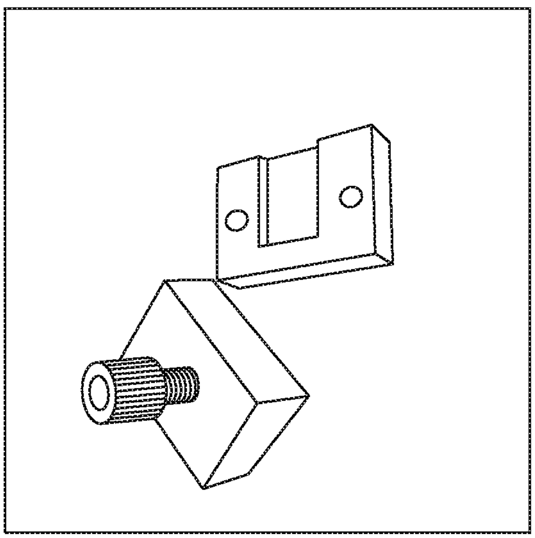
Figure 14A:
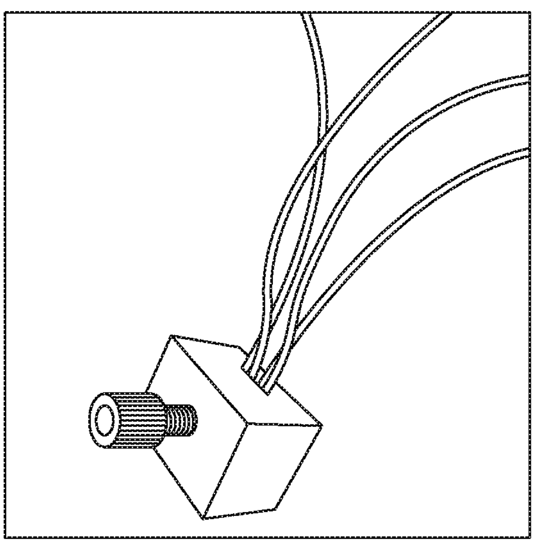

FIG. 13 illustrates a perspective view of another example of the system 102 described above, which includes details regarding certain other system 102 components. For example, a vial tray 142 is shown containing various vials of compounds 144 therein. As described above, gas delivery from the bubbler to the mixing manifold 110 may be conducted via one-way check valves 146. Also, a gas outlet 148 is structured to communicate the flow of a target vapor from the mixing manifold 110 to the sensor 118 for analysis. FIGS. 14A-14C include different views of one example of the sensor 118 (and its various subcomponents) that can be configured for use in connection with various aspects of the system 102 described herein.

Figure 15:
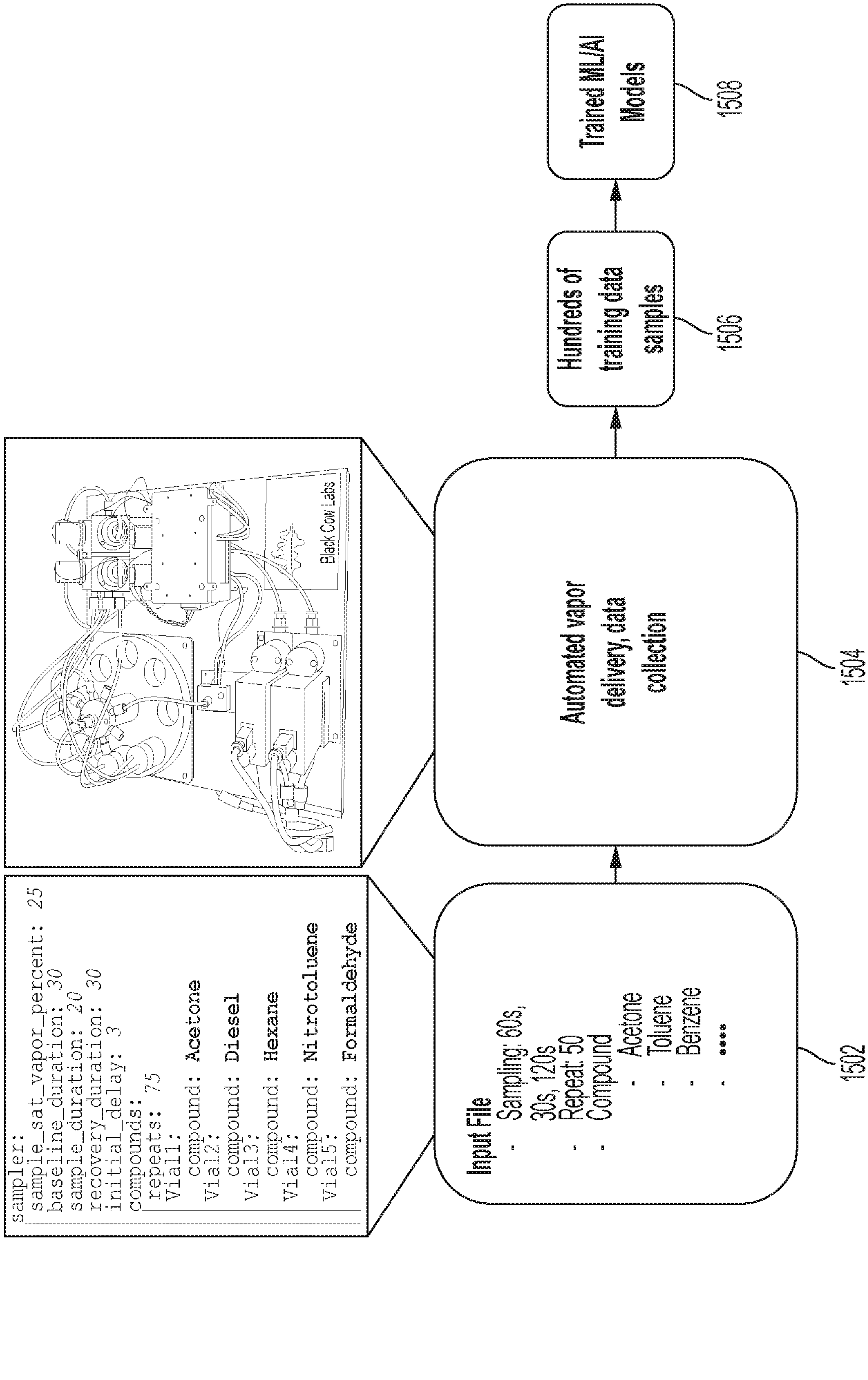
FIG. 15 includes a process flow diagram illustrating examples of processing steps that can be performed in association with an olfactory data processing system.

In operation, and with reference to the process flow diagram in FIG. 15, the system 102 can be programmed for automated execution based on a configuration file or input data file at step 1502. At step 1504 in this example, the system 102 can control its various valves, air flows, MFCs, and other operative components, while also managing data collection, data analysis, and model training. At step 1506, a relatively high volume (e.g., hundreds) of training data samples can be generated by the system 102. At step 1508, the generated data samples can be made part of a data model such as different types of AI/ML models.

Figure 16A:
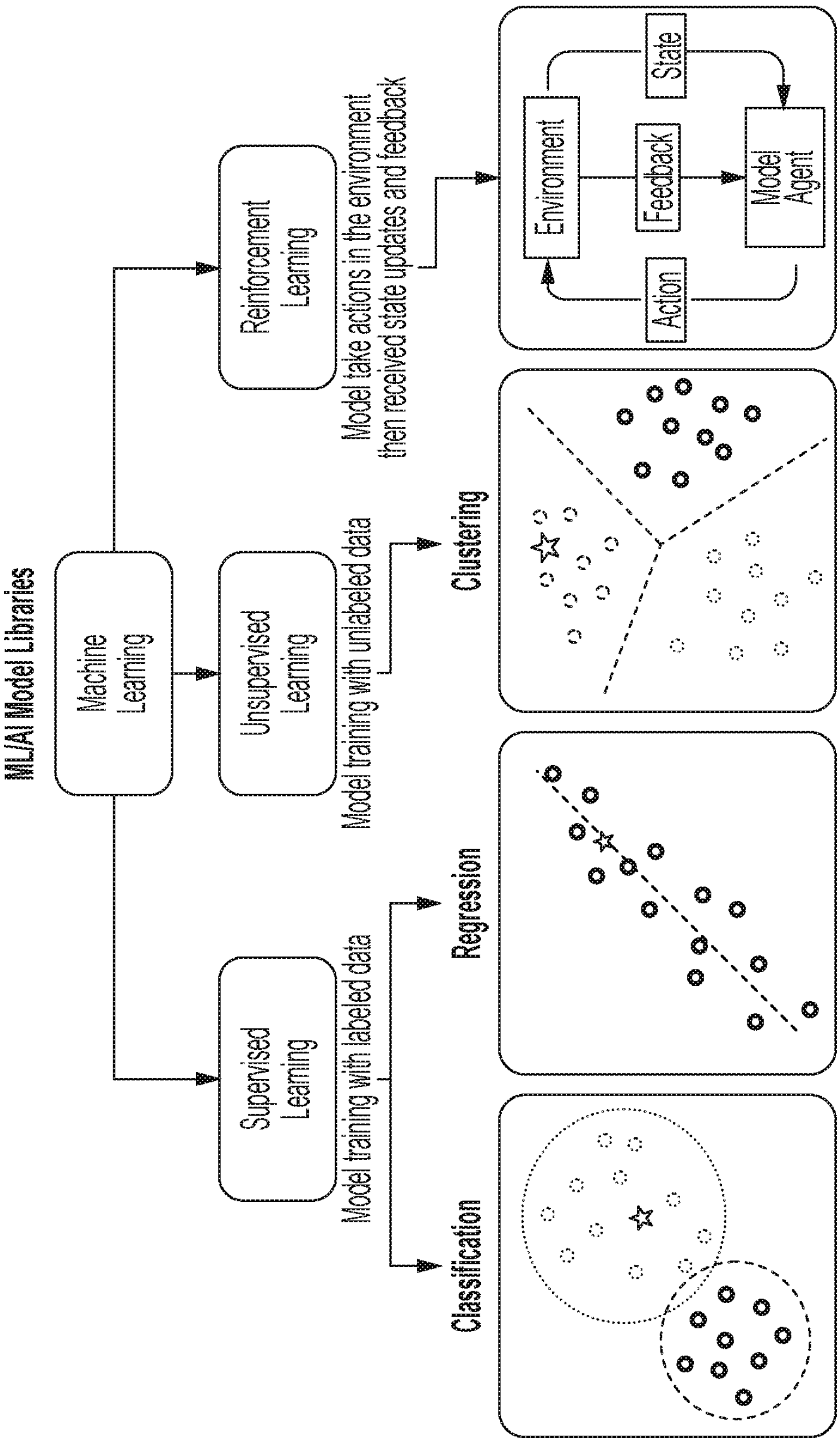
FIG. 16A illustrates how data generated by an olfactory data processing system can be used to enable ML/AI model library creation.
Figure 16B:
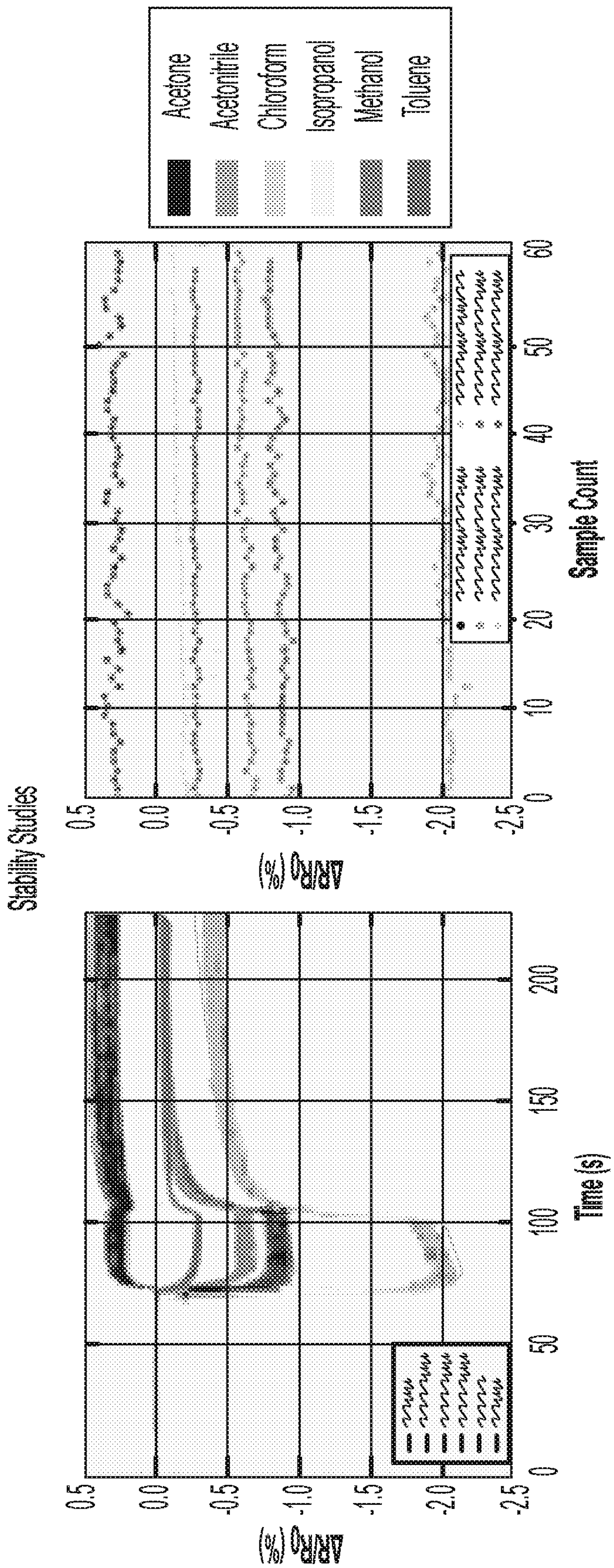
FIG. 16B illustrates how data generated by an olfactory data processing system can be used for stability studies.
Figure 16C:
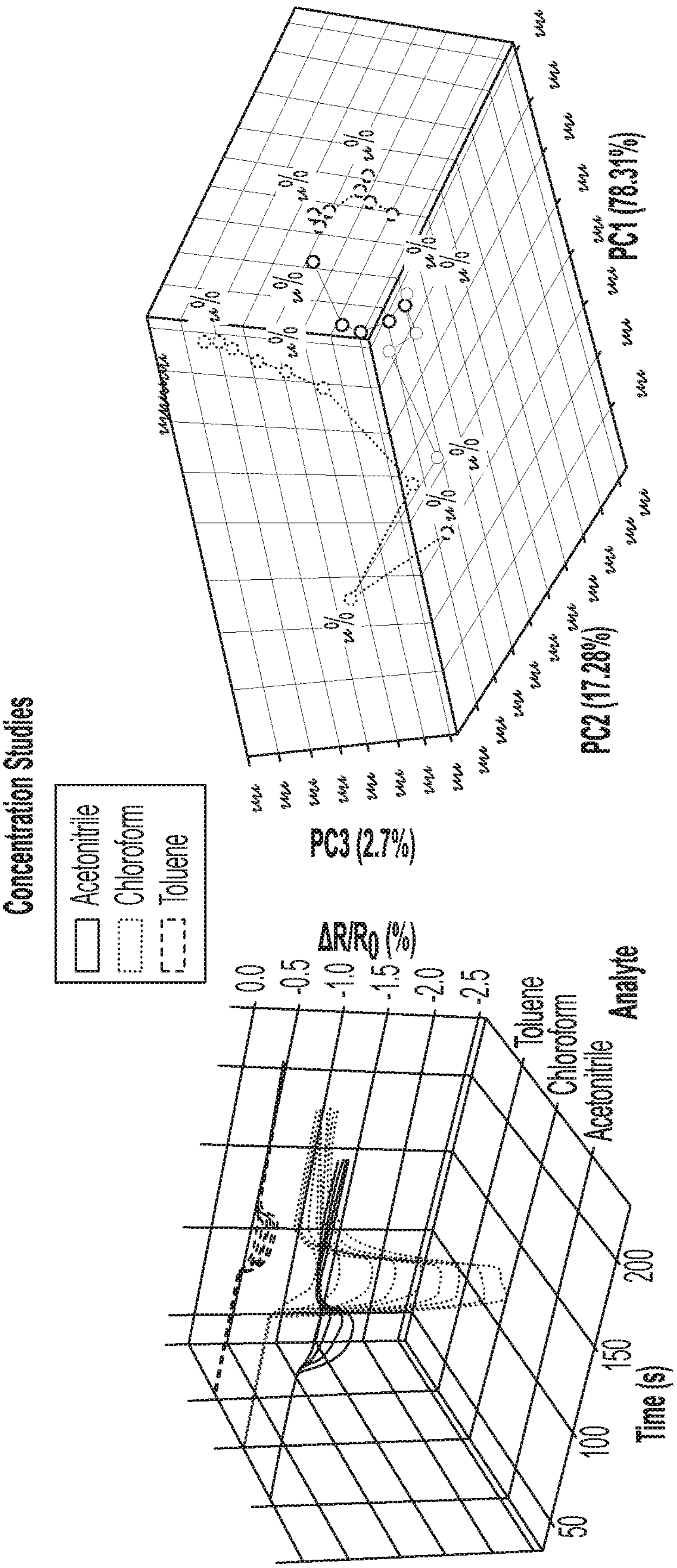
FIG. 16C illustrates how data generated by an olfactory data processing system can be used for concentration studies.

FIG. 16A illustrates how data generated by the system 102 can be used to enable ML/AI model library creation for classification and anomaly detection. Models can be created automatically and/or with a human-in-the-loop. FIG. 16B illustrates how data generated by the system 102 can be used for stability studies. FIG. 16C shows how data generated by the system 102 can be used for concentration studies. The system 102 can facilitate quick retraining to update models based on new compounds or vapors to deploy a new algorithm, versus adding new hardware. Sensor data can be output as graphical representations (e.g., plots) including statistics about sensor response.

Data features can be extracted from time-series sensor responses based on the features described below. Calculated features can be formed into a feature vector and randomized according to each sample row. These sensor profile features can be used as input to feed AI/ML models. Training and test can be divided. The training data set can be used to train and evaluate various AI/ML models. The methods provided herein can be used on datasets ranging from volatile organic compounds, chemical warfare agent simulants, scotch whiskies, essential oils, and many other kinds of chemicals, compounds, and/or odors.

Figure 17:
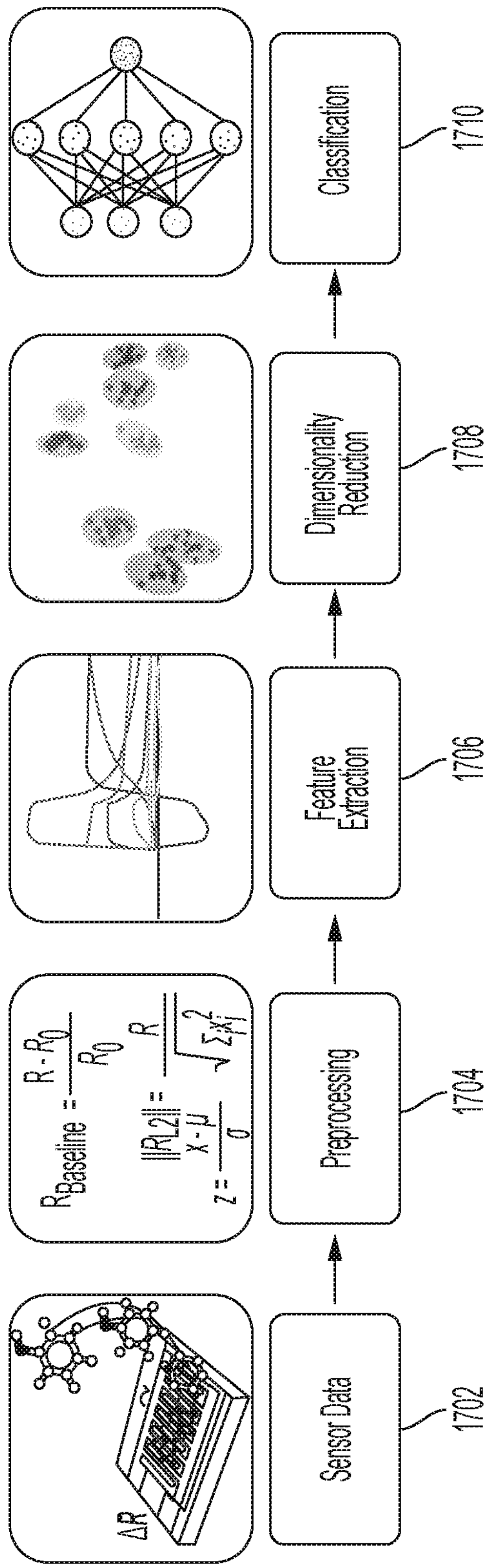
FIG. 17 illustrates a process flow diagram showing one example of processing sensor signature characteristics in accordance with certain embodiments of the present invention.
Figure 18:
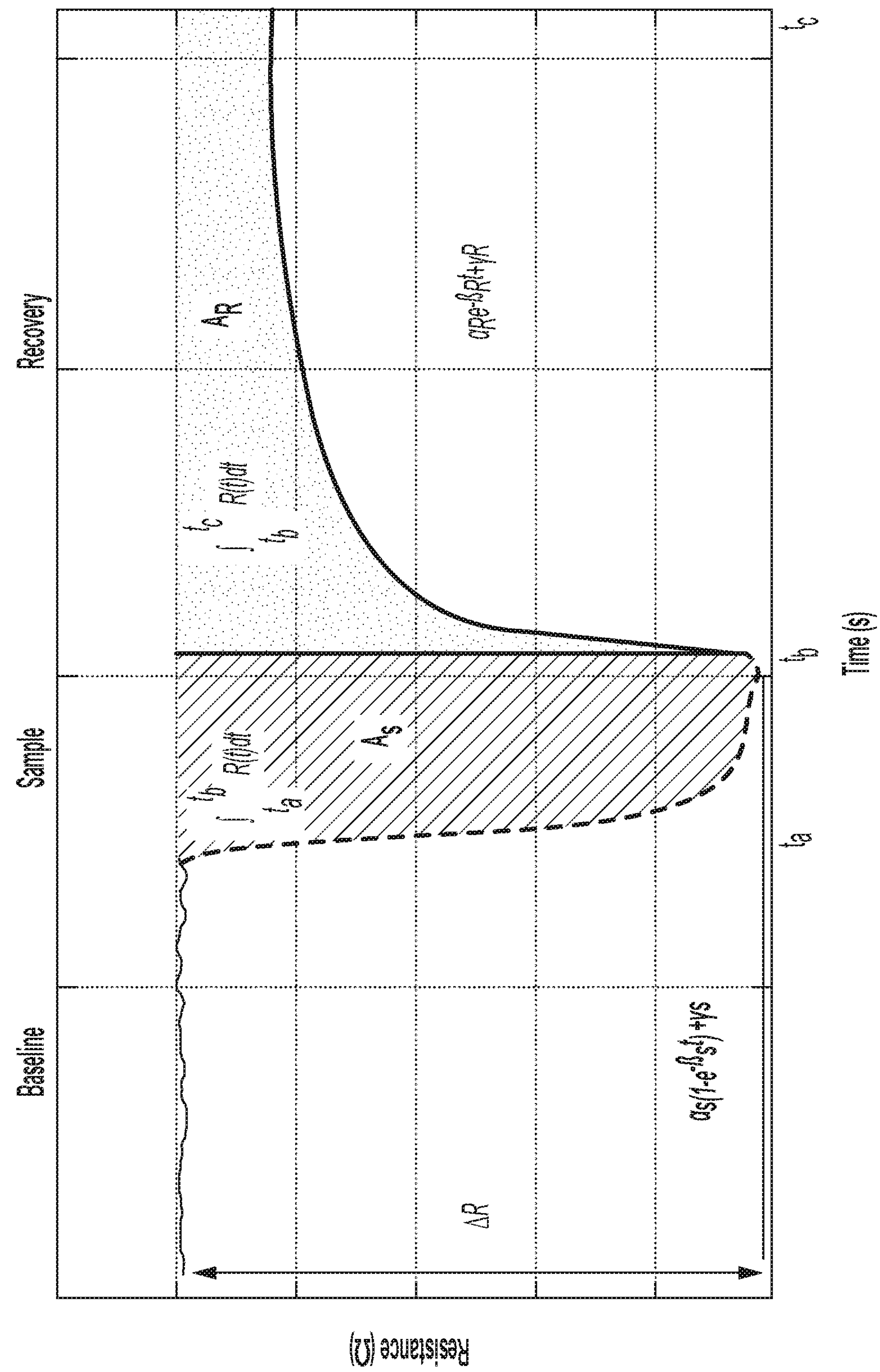
FIG. 18 includes a graphical representation illustrating one example of parametric response features generated in connection with the process flow of FIG. 17.

FIG. 17 illustrates a process flow diagram showing one example of processing sensor signature characteristics in accordance with certain embodiments of the present invention. At step 1702, sensor data can be acquired from one or more sensors. At step 1704, preprocessing of the acquired sensor data may be performed, such as scaling, data transformation, or other data preprocessing activity. At step 1706, feature extraction can be performed. At step 1708, dimensionality reduction can be performed, and at step 1710 classification can be performed. FIG. 18 includes a graphical representation illustrating one example of parametric response features generated in connection with the process flow of FIG. 17. In this example, resistance can be plotted over time and displayed, along with calculations for change in resistance, calculations for area during sampling process, and calculations of area during recovery after the sampling process. In the feature extraction step (1706), features related to analyte-to-surface interaction can be determined, along with sampling process and/or recovery process fitting coefficients.

Figure 19A:
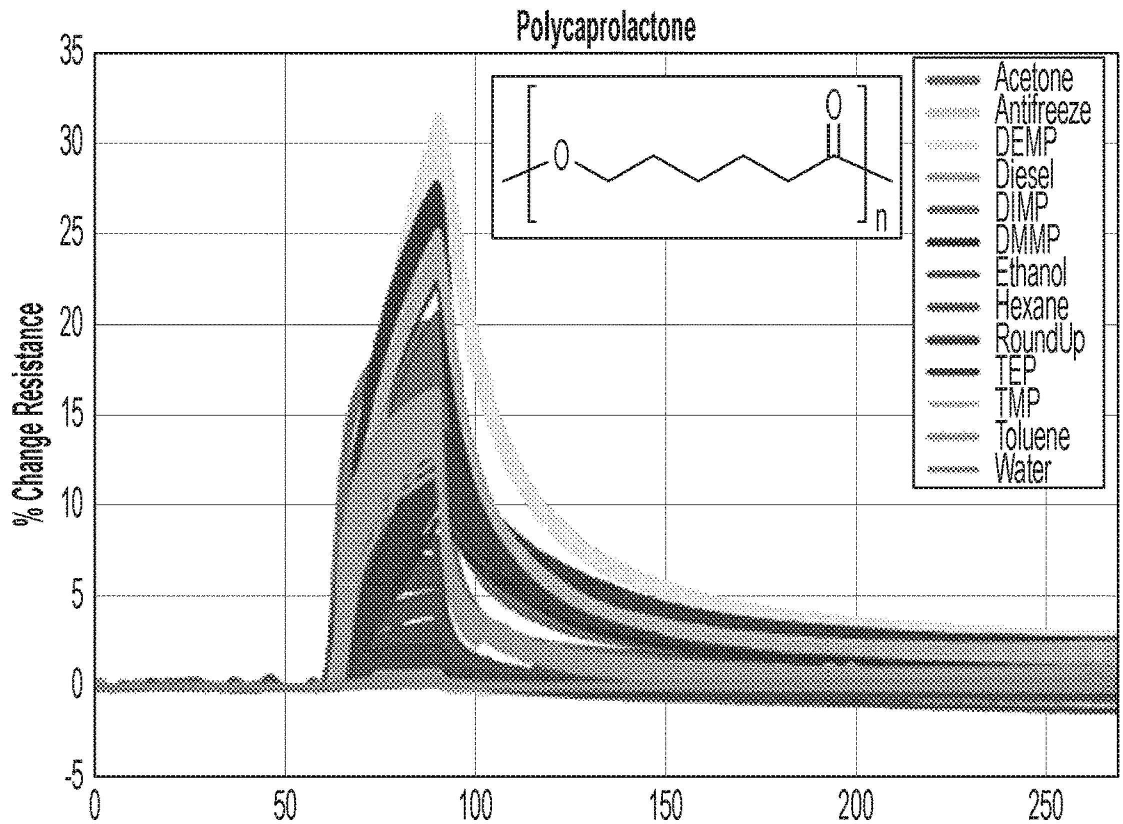
FIGS. 19A-19C illustrate an example of AI/ML model training in connection with warfare agent simulants.
Figure 19B:
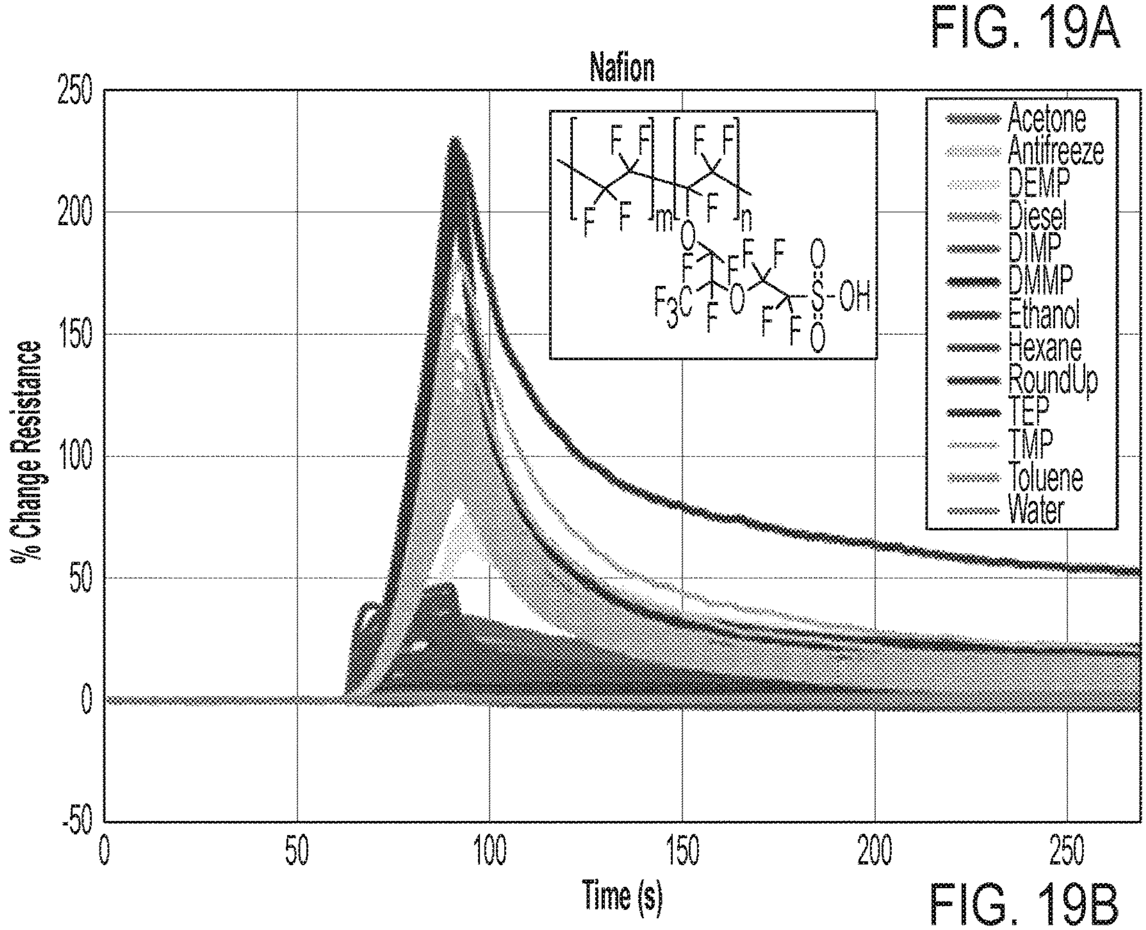
Figure 19C:
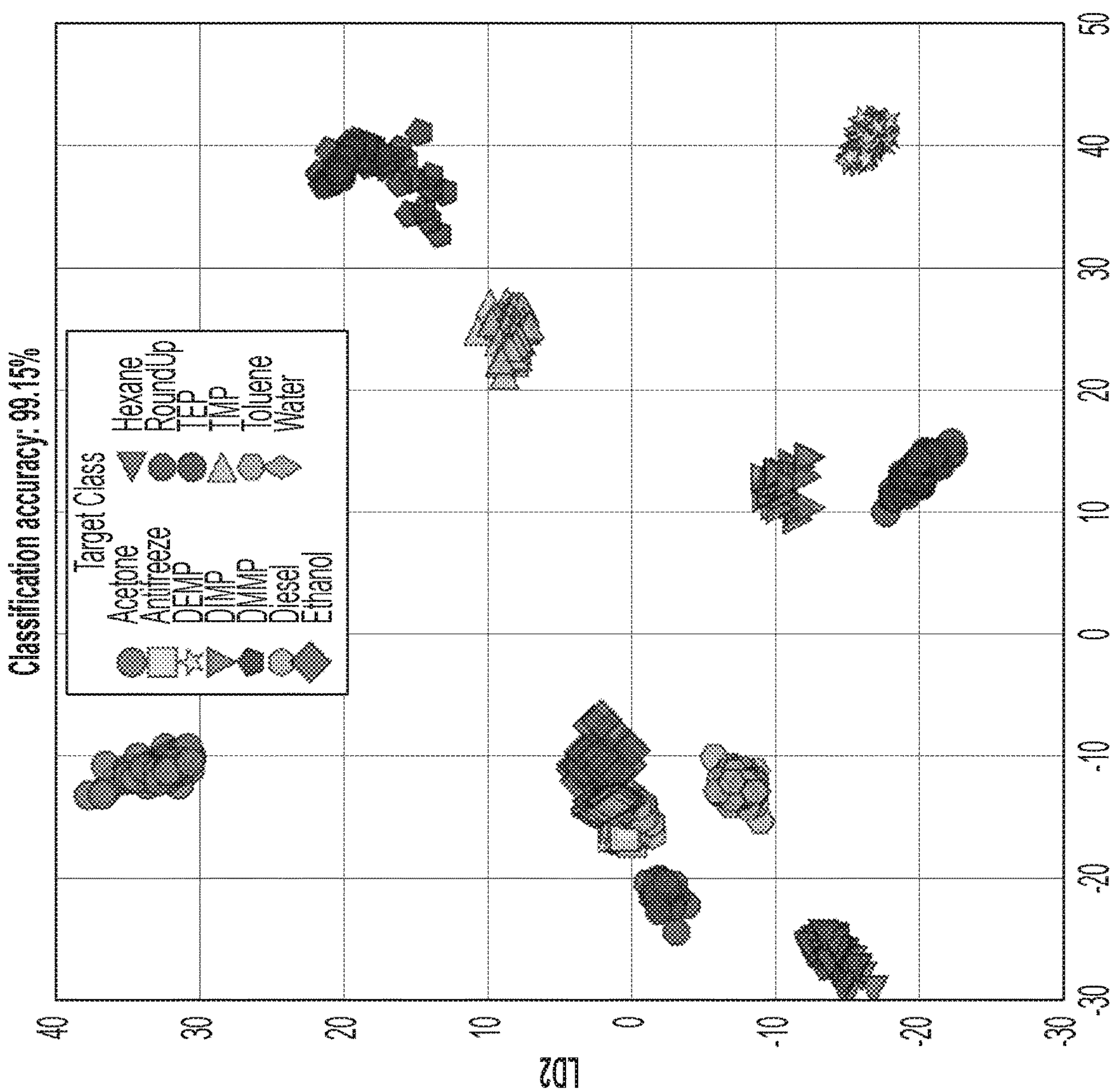

FIGS. 19A-19C illustrate an example of AI/ML model training in connection with warfare agent simulants. In this example, time-series sensor response plots (e.g., for polycaprolactone in FIG. 19A, and for nafion in FIG. 19B) which contain training data can be generated. FIG. 19C illustrates a plot of classification results after the AI/ML model has been trained and used for predictive purposes in this example.

Figure 20A:
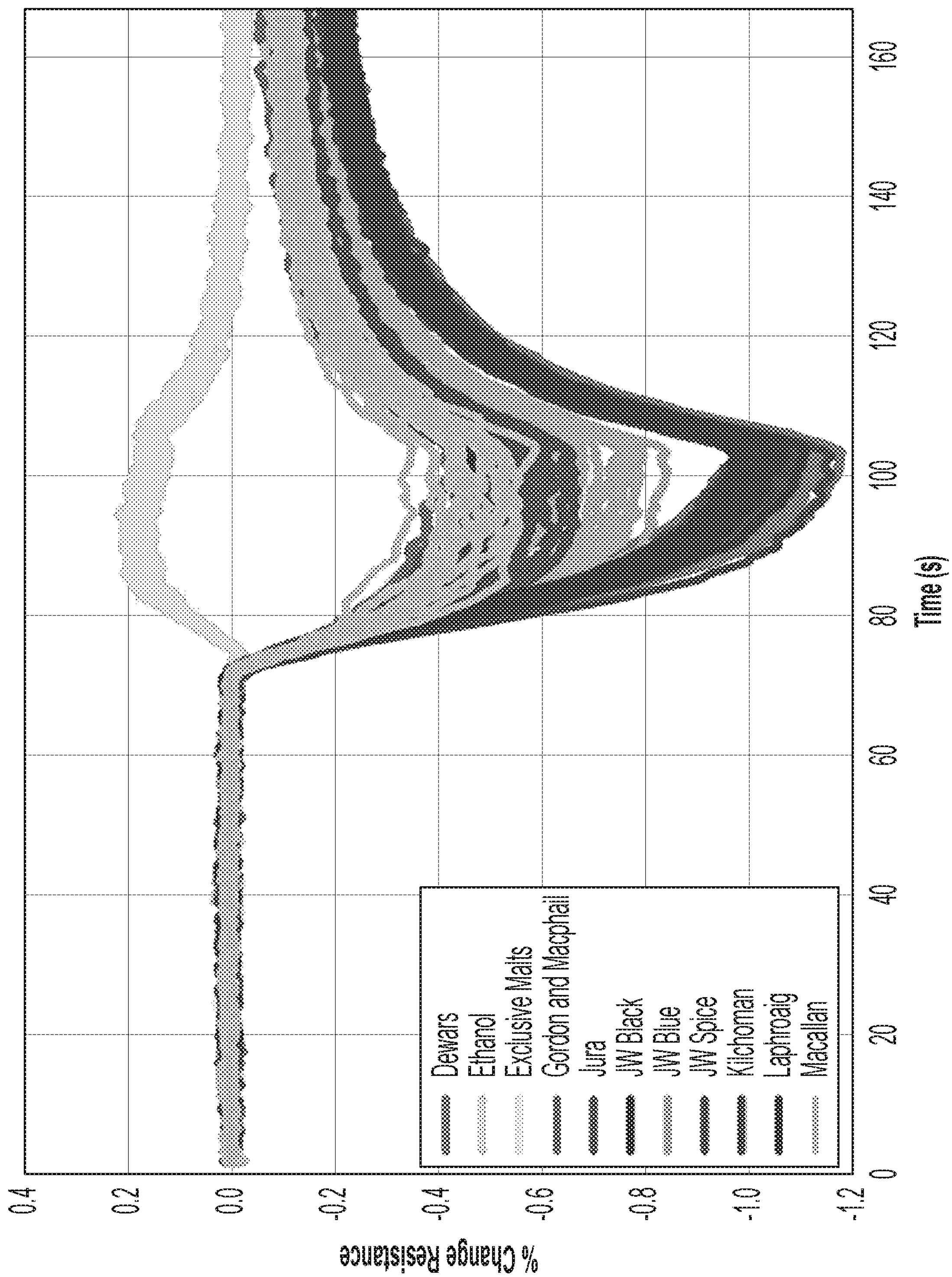
FIGS. 20A and 20B illustrate another example of AI/ML model training in connection with Scotch whiskey.
Figure 20B:
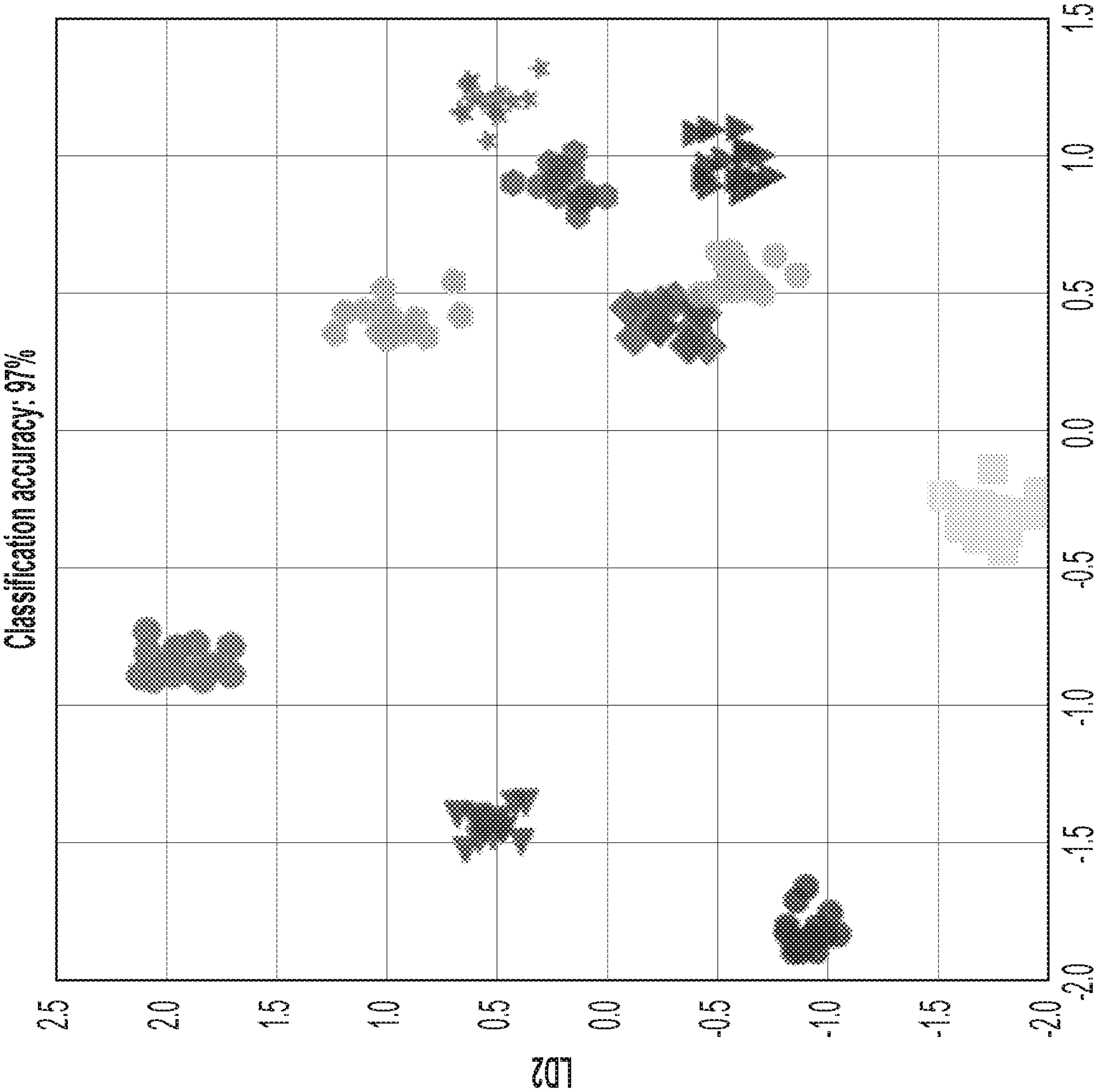

FIGS. 20A and 20B illustrate another example of AI/ML model training in connection with Scotch whiskey. In this example, with reference to FIG. 20A, a time-series sensor response plot (e.g., for various brands of Scotch whiskey) which contains training data can be generated. FIG. 20B illustrates a plot of classification results after the AI/ML model has been trained and used for predictive purposes in this example.

The examples presented herein can be intended to illustrate potential and specific implementations of the present invention. It can be appreciated that the examples can be intended primarily for purposes of illustration of the invention for those skilled in the art. No particular aspect or aspects of the examples can be necessarily intended to limit the scope of the present invention. For example, no particular aspect or aspects of the examples of system architectures, user interface layouts, algorithm use cases, or screen displays described herein can be necessarily intended to limit the scope of the invention.

It is to be understood that the figures and descriptions of the present invention have been simplified to illustrate elements that can be relevant for a clear understanding of the present invention, while eliminating, for purposes of clarity, other elements. Those of ordinary skill in the art will recognize, however, that a sufficient understanding of the present invention can be gained by the present disclosure, and therefore, a more detailed description of such elements is not provided herein.

Any element expressed herein as a means for performing a specified function is intended to encompass any way of performing that function including, for example, a combination of elements that performs that function. Furthermore, the invention as may be defined by such means-plus-function claims, resides in the fact that the functionalities provided by the various recited means can be combined and brought together in a manner as defined by the appended claims. Therefore, any means that can provide such functionalities may be considered equivalents to the means shown herein.

In various embodiments, modules or software can be used to practice certain aspects of the invention. For example, software-as-a-service (SaaS) models or application service provider (ASP) models may be employed as software application delivery models to communicate software applications to clients or other users. Such software applications can be downloaded through an Internet connection, for example, and operated either independently (e.g., downloaded to a laptop or desktop computer system) or through a third-party service provider (e.g., accessed through a third-party web site). In addition, cloud computing techniques may be employed in connection with various embodiments of the invention.

Moreover, the processes associated with the present embodiments may be executed by programmable equipment, such as computers. Software or other sets of instructions that may be employed to cause programmable equipment to execute the processes may be stored in any storage device, such as a computer system (non-volatile) memory. Furthermore, some of the processes may be programmed when the computer system is manufactured or via a computer-readable memory storage medium.

It can also be appreciated that certain process aspects described herein may be performed using instructions stored on a computer-readable memory medium or media that direct a computer or computer system to perform process steps. A computer-readable medium may include, for example, memory devices such as diskettes, compact discs of both read-only and read/write varieties, optical disk drives, and hard disk drives. A computer-readable medium may also include memory storage that may be physical, virtual (e.g., cloud-based), permanent, temporary, semi-permanent and/or semi-temporary. Memory and/or storage components may be implemented using any computer-readable media capable of storing data such as volatile or non-volatile memory, removable or non-removable memory, erasable or non-erasable memory, writeable or re-writeable memory, and so forth.

Examples of computer-readable storage media may include, without limitation, RAM, dynamic RAM (DRAM), Double-Data-Rate DRAM (DDRAM), synchronous DRAM (SDRAM), static RAM (SRAM), read-only memory (ROM), programmable ROM (PROM), erasable programmable ROM (EPROM), electrically erasable programmable ROM (EEPROM), flash memory (e.g., NOR or NAND flash memory), content addressable memory (CAM), polymer memory (e.g., ferroelectric polymer memory), phase-change memory, ovonic memory, ferroelectric memory, silicon-oxide-nitride-oxide-silicon (SONOS) memory, magnetic or optical cards, or any other type of media suitable for storing information.

A "computer," "computer system," "computing apparatus," "component," or "computer processor" may be, for example and without limitation, a processor, microcomputer, minicomputer, server, mainframe, laptop, personal data assistant (PDA), wireless e-mail device, smart phone, mobile phone, electronic tablet, cellular phone, pager, processor, fax machine, scanner, or any other programmable device or computer apparatus configured to transmit, process, and/or receive data. Computer systems and computer-based devices disclosed herein may include memory and/or storage components for storing certain software applications used in obtaining, processing, and communicating information. It can be appreciated that such memory may be internal or external with respect to execution of the disclosed embodiments. In various embodiments, a "host," "engine," "loader," "filter," "platform," or "component" may include various computers or computer systems, or may include a reasonable combination of software, firmware, and/or hardware. In certain embodiments, a "module" may include software, firmware, hardware, or any reasonable combination thereof.

In various embodiments of the present invention, a single component may be replaced by multiple components, and multiple components may be replaced by a single component, to perform a given function or functions. Except where such substitution would not be operative to practice embodiments of the present invention, such substitution is within the scope of the present invention. Any of the servers described herein, for example, may be replaced by a "server farm" or other grouping of networked servers (e.g., a group of server blades) that can be located and configured for cooperative functions. It can be appreciated that a server farm may serve to distribute workload between/among individual components of the farm and may expedite computing processes by harnessing the collective and cooperative power of multiple servers. Such server farms may employ load-balancing software that accomplishes tasks such as, for example, tracking demand for processing power from different machines, prioritizing and scheduling tasks based on network demand, and/or providing backup contingency in the event of component failure or reduction in operability.

In general, it will be apparent to one of ordinary skill in the art that various embodiments described herein, or components or parts thereof, may be implemented in many different embodiments of software, firmware, and/or hardware, or modules thereof. The software code or specialized control hardware used to implement some of the present embodiments is not limiting of the present invention. For example, the embodiments described hereinabove may be implemented in computer software using any suitable computer programming language such as .NET or HTML using, for example, conventional or object-oriented techniques. Programming languages for computer software and other computer-implemented instructions may be translated into machine language by a compiler or an assembler before execution and/or may be translated directly at run time by an interpreter. Examples of assembly languages include ARM, MIPS, and x86; examples of high-level languages include Ada, BASIC, C, C++, C#, COBOL, Fortran, Java, Lisp, Pascal, Object Pascal; and examples of scripting languages include Bourne script, JavaScript, Python, TypeScript, Ruby, PHP, and Perl. Various embodiments may be employed in a Lotus Notes environment, for example. Such software may be stored on any type of suitable computer-readable medium or media such as, for example, a magnetic or optical storage medium.

Thus, the execution and behavior of the embodiments can be described without specific reference to the actual software code. The absence of such specific references is feasible because it is clearly understood that artisans of ordinary skill would be able to design software and control hardware to implement the embodiments of the present invention based on the description herein with only a reasonable effort and without undue experimentation.

Various embodiments of the systems and methods described herein may employ one or more electronic computer networks to promote communication among different components, transfer data, or to share resources and information. Such computer networks can be classified according to the hardware and software technology that is used to interconnect the devices in the network, such as optical fiber, Ethernet, wireless LAN, HomePNA, cellular network communication, power line communication, or G.hn. The computer networks may also be embodied as one or more of the following types of networks: local area network (LAN); metropolitan area network (MAN); wide area network (WAN); virtual private network (VPN); storage area network (SAN); or global area network (GAN), among other network varieties.

For example, a WAN computer network may cover a broad area by linking communications across metropolitan, regional, or national boundaries. The network may use routers and/or public communication links. One type of data communication network may cover a relatively broad geographic area (e.g., city-to-city or country-to-country) which uses transmission facilities provided by common carriers, such as telephone service providers. In another example, a GAN computer network may support mobile communications across multiple wireless LANs or satellite networks. In another example, a VPN computer network may include links between nodes carried by open connections or virtual circuits in another network (e.g., the Internet) instead of by physical wires. The link-layer protocols of the VPN can be tunneled through the other network. One VPN application can promote secure communications through the Internet. The VPN can also be used to separately and securely conduct the traffic of different user communities over an underlying network. The VPN may provide users with the virtual experience of accessing the network through an IP address location other than the actual IP address which connects the access device to the network.

The computer network may be characterized based on functional relationships among the elements or components of the network, such as active networking, client-server, or peer-to-peer functional architecture. The computer network may be classified according to network topology, such as bus network, star network, ring network, mesh network, star-bus network, or hierarchical topology network, for example. The computer network may also be classified based on the method employed for data communication, such as digital and analog networks.

Embodiments of the methods and systems described herein may employ internetworking for connecting two or more distinct electronic computer networks or network segments through a common routing technology. The type of internetwork employed may depend on administration and/or participation in the internetwork. Non-limiting examples of internetworks include intranet, extranet, and Internet. Intranets and extranets may or may not have connections to the Internet. If connected to the Internet, the intranet or extranet may be protected with appropriate authentication technology or other security measures. As applied herein, an intranet can be a group of networks which employ Internet Protocol, web browsers and/or file transfer applications, under common control by an administrative entity. Such an administrative entity could restrict access to the intranet to only authorized users, for example, or another internal network of an organization or commercial entity. As applied herein, an extranet may include a network or internetwork generally limited to a primary organization or entity, but which also has limited connections to the networks of one or more other trusted organizations or entities (e.g., customers of an entity may be given access an intranet of the entity thereby creating an extranet).

Computer networks may include hardware elements to interconnect network nodes, such as network interface cards (NICs) or Ethernet cards, repeaters, bridges, hubs, switches, routers, and other like components. Such elements may be physically wired for communication and/or data connections may be provided with microwave links (e.g., IEEE 802.12) or fiber optics, for example. A network card, network adapter or NIC can be designed to allow computers to communicate over the computer network by providing physical access to a network and an addressing system through the use of MAC addresses, for example. A repeater can be embodied as an electronic device that receives and retransmits a communicated signal at a boosted power level to allow the signal to cover a telecommunication distance with reduced degradation. A network bridge can be configured to connect multiple network segments at the data link layer of a computer network while learning which addresses can be reached through which specific ports of the network. In the network, the bridge may associate a port with an address and then send traffic for that address only to that port. In various embodiments, local bridges may be employed to directly connect local area networks (LANs). Remote bridges can be used to create a wide area network (WAN) link between LANs; and/or, wireless bridges can be used to connect LANs and/or to connect remote stations to LANs.

In various embodiments, a hub may be employed which contains multiple ports. For example, when a data packet arrives at one port of a hub, the packet can be copied unmodified to all ports of the hub for transmission. A network switch or other devices that forward and filter OSI layer 2 datagrams between ports based on MAC addresses in data packets can also be used. A switch can possess multiple ports, such that most of the network is connected directly to the switch, or another switch that is in turn connected to a switch. The term “switch” can also include routers and bridges, as well as other devices that distribute data traffic by application content (e.g., a Web URL identifier). Switches may operate at one or more OSI model layers, including physical, data link, network, or transport (i.e., end-to-end). A device that operates simultaneously at more than one of these layers can be considered a multilayer switch. In certain embodiments, routers or other like networking devices may be used to forward data packets between networks using headers and forwarding tables to determine an optimum path through which to transmit the packets.

As employed herein, an application server may be a server that hosts an API to expose business logic and business processes for use by other applications. Examples of application servers include J2EE or Java EE 5 (Oracle) application servers including WebSphere Application Server. Other examples include WebSphere Application Server Community Edition (IBM), Sybase Enterprise Application Server (Sybase Inc), WebLogic Server (BEA), JBoss (Red Hat), JRun (Adobe Systems), Apache Geronimo (Apache Software Foundation), Oracle OC4J (Oracle Corporation), Sun Java System Application Server (Sun Microsystems), and SAP Netweaver AS (ABAP/Java). Also, application servers may be provided in accordance with the .NET framework, including the Windows Communication Foundation, .NET Remoting, ADO.NET, and ASP.NET among several other components. For example, a Java Server Page (JSP) is a servlet that executes in a web container which is functionally equivalent to CGI scripts. JSPs can be used to create HTML pages by embedding references to the server logic within the page. The application servers may mainly serve web-based applications, while other servers can perform as session initiation protocol servers, for instance, or work with telephony networks. Specifications for enterprise application integration and service-oriented architecture can be designed to connect many different computer network elements. Such specifications include Business Application Programming Interface, Web Services Interoperability, and Java EE Connector Architecture. Certain embodiments of the invention may employ web servers such as Apache web servers, for example.

Embodiments of the methods and systems described herein may divide functions between separate CPUs, creating a multiprocessing configuration. For example, multiprocessor and multi-core (multiple CPUs on a single integrated circuit) computer systems with co-processing capabilities may be employed. Also, multitasking may be employed as a computer processing technique to handle simultaneous execution of multiple computer programs.

In various embodiments, the computer systems, data storage media, or modules described herein may be configured and/or programmed to include one or more of the above-described electronic, computer-based elements and components, or computer architecture. In addition, these elements and components may be particularly configured to execute the various rules, algorithms, programs, processes, and method steps described herein.

Various embodiments may be described herein in the general context of computer executable instructions, such as software, program modules, and/or engines being executed by a computer. Generally, software, program modules, and/or engines include any software element arranged to perform particular executions or implement particular abstract data types. Software, program modules, and/or engines can include routines, programs, objects, components, data structures and the like that perform particular tasks or implement particular abstract data types. An implementation of the software, program modules, and/or engines components and techniques may be stored on and/or transmitted across some form of computer-readable media. In this regard, computer-readable media can be any available medium or media useable to store information and accessible by a computing device. Some embodiments also may be practiced in distributed computing environments where executions can be performed by one or more remote processing devices that can be linked through a communications network. In a distributed computing environment, software, program modules, and/or engines may be located in both local and remote computer storage media including memory storage devices.

Although some embodiments may be illustrated and described as comprising functional components, software, engines, and/or modules performing various executions, it can be appreciated that such components or modules may be implemented by one or more hardware components, software components, and/or combination thereof. The functional components, software, engines, and/or modules may be implemented, for example, by logic (e.g., instructions, data, and/or code) to be executed by a logic device (e.g., processor). Such logic may be stored internally or externally to a logic device on one or more types of computer-readable storage media. In other embodiments, the functional components such as software, engines, and/or modules may be implemented by hardware elements that may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Examples of software, engines, and/or modules may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof.

Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

In some cases, various embodiments may be implemented as an article of manufacture. The article of manufacture may include a computer readable storage medium arranged to store logic, instructions and/or data for performing various executions of one or more embodiments. In various embodiments, for example, the article of manufacture may comprise a magnetic disk, optical disk, flash memory or firmware containing computer program instructions suitable for execution by an application specific processor.

Additionally, it is to be appreciated that the embodiments described herein illustrate example implementations, and that the functional elements, logical blocks, modules, and circuits elements may be implemented in various other ways which can be consistent with the described embodiments. Furthermore, the executions performed by such functional elements, logical blocks, modules, and circuits elements may be combined and/or separated for a given implementation and may be performed by a greater number or fewer number of components or modules. As will be apparent to those of skill in the art upon reading the present disclosure, each of the individual embodiments described and illustrated herein has discrete components and features which may be readily separated from or combined with the features of any of the other several aspects without departing from the scope of the present disclosure. Any recited method can be carried out in the order of events recited or in any other order which is logically possible.

Reference to "one embodiment" or "an embodiment" means that a particular feature, structure, or characteristic described in connection with the embodiment is comprised in at least one embodiment. The appearances of the phrase "in one embodiment" or "in one aspect" in the specification can be not necessarily all referring to the same embodiment.

Unless specifically stated otherwise, it may be appreciated that terms such as "processing," "computing," "calculating," "determining," or the like, refer to the action and/or processes of a computer or computing system, or similar electronic computing device, such as a general purpose processor, a DSP, ASIC, FPGA or other programmable logic device, discrete gate or transistor logic, discrete hardware components, or any combination thereof designed to perform the functions described herein that manipulates and/or transforms data represented as physical quantities (e.g., electronic) within registers and/or memories into other data similarly represented as physical quantities within the memories, registers or other such information storage, transmission or display devices.

Certain embodiments may be described using the expression "coupled" and "connected" along with their derivatives. These terms can be not necessarily intended as synonyms for each other. For example, some embodiments may be described using the terms "connected" and/or "coupled" to indicate that two or more elements can be in direct physical or electrical contact with each other. The term "coupled," however, also may mean that two or more elements can be not in direct contact with each other, but yet still co-operate or interact with each other. With respect to software elements, for example, the term "coupled" may refer to interfaces, message interfaces, application program interface (API), exchanging messages, and so forth.

It will be appreciated that those skilled in the art will be able to devise various arrangements which, although not explicitly described or shown herein, embody the principles of the present disclosure and can be comprised within the scope thereof. Furthermore, all examples and conditional language recited herein can be principally intended to aid the reader in understanding the principles described in the present disclosure and the concepts contributed to furthering the art, and can be to be construed as being without limitation to such specifically recited examples and conditions. Moreover, all statements herein reciting principles, aspects, and embodiments as well as specific examples thereof, can be intended to encompass both structural and functional equivalents thereof. Additionally, it is intended that such equivalents comprise both currently known equivalents and equivalents developed in the future, i.e., any elements developed that perform the same function, regardless of structure. The scope of the present disclosure, therefore, is not intended to be limited to the exemplary aspects and aspects shown and described herein.

Although various systems described herein may be embodied in software or code executed by general purpose hardware as discussed above, as an alternative the same may also be embodied in dedicated hardware or a combination of software, hardware and/or dedicated hardware. If embodied in dedicated hardware, each can be implemented as a circuit or state machine that employs any one of or a combination of a number of technologies. These technologies may include, but can be not limited to, discrete logic circuits having logic gates for implementing various logic functions upon an application of one or more data signals, application specific integrated circuits having appropriate logic gates, or other components, etc. Such technologies can be generally well known by those of ordinary skill in the art and, consequently, may not be described in detail herein.

The flow charts and methods described herein show the functionality and execution of various implementations. If embodied in software, each block, step, or action may represent a module, segment, or portion of code that comprises program instructions to implement the specified logical function(s). The program instructions may be embodied in the form of source code that comprises human-readable statements written in a programming language or machine code that comprises numerical instructions recognizable by a suitable execution system such as a processing component in a computer system. If embodied in hardware, each block may represent a circuit or a number of interconnected circuits to implement the specified logical function(s). Although the flow charts and methods described herein may describe a specific order of execution, it is understood that the order of execution may differ from that which is described. For example, the order of execution of two or more blocks or steps may be scrambled relative to the order described. Also, two or more blocks or steps may be executed concurrently or with partial concurrence. Further, in some embodiments, one or more of the blocks or steps may be omitted or not performed. It is understood that all such variations can be within the scope of the present disclosure.

The terms "a" and "an" and "the" and similar referents used in the context of the present disclosure (especially in the context of the following claims) can be to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as though it were individually recited herein. All methods described herein can be performed in any suitable order unless otherwise indicated herein or otherwise clearly contradicted by context. The use of any and all examples, or exemplary language (e.g., "such as," "in the case," "by way of example") provided herein is intended merely to better illuminate the disclosed embodiments and does not pose a limitation on the scope otherwise claimed. No language in the specification should be construed as indicating any non-claimed element essential to the practice of the claimed subject matter. It is further noted that the claims may be drafted to exclude any optional element. As such, this statement is intended to serve as antecedent basis for use of such exclusive terminology as solely, only and the like in connection with the recitation of claim elements, or use of a negative limitation.

Groupings of alternative elements or embodiments disclosed herein can be not to be construed as limitations. Each group member may be referred to and claimed individually or in any combination with other members of the group or other elements found herein. It is anticipated that one or more members of a group may be comprised in, or deleted from, a group for reasons of convenience and/or patentability.

In various embodiments of the present invention, different types of artificial intelligence tools and techniques can be incorporated and implemented. Search and optimization tools including search algorithms, mathematical optimization, and evolutionary computation methods can be used for intelligently searching through many possible solutions. For example, logical operations can involve searching for a path that leads from premises to conclusions, where each step is the application of an inference rule. Planning algorithms can search through trees of goals and subgoals, attempting to find a path to a target goal, in a process called means-ends analysis.

Heuristics can be used to prioritize choices in favor of those more likely to reach a goal and to do so in a shorter number of steps. In some search methodologies heuristics can also serve to eliminate some choices unlikely to lead to a goal. Heuristics can supply a computer system with a best estimate for the path on which the solution lies. Heuristics can limit the search for solutions into a smaller sample size, thereby increasing overall computer system processing efficiency.

Propositional logic can be used which involves truth functions such as "or" and "not" search terms, and first-order logic can add quantifiers and predicates, and can express facts about objects, their properties, and their relationships with each other. Fuzzy logic assigns a degree of truth (e.g., between 0 and 1) to vague statements which may be too linguistically imprecise to be completely true or false. Default logics, non-monotonic logics and circumscription are forms of logic designed to help with default reasoning and the qualification problem. Several extensions of logic can be used to address specific domains of knowledge, such as description logics, situation calculus, event calculus and fluent calculus (for representing events and time), causal calculus, belief calculus (belief revision); and modal logics. Logic for modeling contradictory or inconsistent statements arising in multi-agent systems can also be used, such as paraconsistent logics.

Probabilistic methods can be applied for uncertain reasoning, such as Bayesian networks, hidden Markov models, Kalman filters, particle filters, decision theory, and utility theory. These tools and techniques help the system execute algorithms with incomplete or uncertain information. Bayesian networks are tools that can be used for various problems: reasoning (using the Bayesian inference algorithm), learning (using the expectation-maximization algorithm), planning (using decision networks), and perception (using dynamic Bayesian networks). Probabilistic algorithms can be used for filtering, prediction, smoothing and finding explanations for streams of data, helping perception systems to analyze processes that occur over time (e.g., hidden Markov models or Kalman filters). Artificial intelligence can use the concept of utility as a measure of how valuable something is to an intelligent agent. Mathematical tools can analyze how an agent can make choices and plan, using decision theory, decision analysis, and information value theory. These tools include models such as Markov decision processes, dynamic decision networks, game theory and mechanism design.

The artificial intelligence techniques applied to embodiments of the invention may leverage classifiers and controllers. Classifiers are functions that use pattern matching to determine a closest match. They can be tuned according to examples known as observations or patterns. In supervised learning, each pattern belongs to a certain predefined class which represents a decision to be made. All of the observations combined with their class labels are known as a data set. When a new observation is received, that observation is classified based on previous experience. A classifier can be trained in various ways; there are many statistical and machine learning approaches. The decision tree is one kind of symbolic machine learning algorithm. The naive Bayes classifier is one kind of classifier useful for its scalability, in particular. Neural networks can also be used for classification. Classifier performance depends in part on the characteristics of the data to be classified, such as the data set size, distribution of samples across classes, dimensionality, and the level of noise. Model-based classifiers perform optimally when the assumed model is an optimized fit for the actual data. Otherwise, if no matching model is available, and if accuracy (rather than speed or scalability) is a primary concern, then discriminative classifiers (e.g., SVM) can be used to enhance accuracy.

A neural network is an interconnected group of nodes which can be used in connection with various embodiments of the invention, such as execution of various methods, processes, or algorithms disclosed herein. Each neuron of the neural network can accept inputs from other neurons, each of which when activated casts a weighted vote for or against whether the first neuron should activate. Learning achieved by the network involves using an algorithm to adjust these weights based on the training data. For example, one algorithm increases the weight between two connected neurons when the activation of one triggers the successful activation of another. Neurons have a continuous spectrum of activation, and neurons can process inputs in a non-linear way rather than weighing straightforward votes. Neural networks can model complex relationships between inputs and outputs or find patterns in data. They can learn continuous functions and even digital logical operations. Neural networks can be viewed as a type of mathematical optimization which performs a gradient descent on a multi-dimensional topology that was created by training the network. Another type of algorithm is a backpropagation algorithm. Other examples of learning techniques for neural networks include Hebbian learning, group method of data handling (GMDH), or competitive learning. The main categories of networks are acyclic or feedforward neural networks (where the signal passes in only one direction), and recurrent neural networks (which allow feedback and short-term memories of previous input events). Examples of feedforward networks include perceptrons, multi-layer perceptrons, and radial basis networks.

Deep learning techniques applied to various embodiments of the invention can use several layers of neurons between the network's inputs and outputs. The multiple layers can progressively extract higher-level features from the raw input. For example, in image processing, lower layers may identify edges, while higher layers may identify the concepts relevant to a human such as digits or letters or faces. Deep learning may involve convolutional neural networks for many or all of its layers. In a convolutional layer, each neuron receives input from only a restricted area of the previous layer called the neuron's receptive field. This can substantially reduce the number of weighted connections between neurons. In a recurrent neural network, the signal will propagate through a layer more than once. A recurrent neural network (RNN) is another example of a deep learning technique which can be trained by gradient descent, for example.

While various embodiments of the invention have been described herein, it should be apparent, however, that various modifications, alterations, and adaptations to those embodiments may occur to persons skilled in the art with the attainment of some or all of the advantages of the present invention. The disclosed embodiments are therefore intended to include all such modifications, alterations, and adaptations without departing from the scope and spirit of the present invention as claimed herein.

What is claimed is:

1. A computer-implemented olfactory data processing system comprising:

a system controller programmed for:

controlling at least one function of multiple components of the computer-implemented olfactory data processing system;

selecting at least one vial containing a predetermined compound;

activating a relay to transmit the predetermined compound in the selected at least one vial to a mixing manifold;

directing at least one mass flow controller (MFC) for processing a sample of the predetermined compound;

the mixing manifold configured for processing the predetermined compound to produce a target vapor as a test sample for analysis; and a sensor configured for sensing at least one olfactory attribute of the test sample.

2. The computer-implemented olfactory data processing system of claim 1, further comprising a data acquisition module, operatively associated with the system controller, programmed for receiving signals communicated from the sensor indicative of sensor data.

3. The computer-implemented olfactory data processing system of claim 1, wherein at least one relay comprises a web relay.

4. The computer-implemented olfactory data processing system of claim 3, further comprising the web relay programmed for connecting to a web-based application for receiving collected sensor data.

5. The computer-implemented olfactory data processing system of claim 4, further comprising the system controller programmed for performing automated collection of the sensor data.

6. The computer-implemented olfactory data processing system of claim 3, further comprising at least one solenoid operatively connected to the web relay, the at least one solenoid corresponding to a single relay and a single bubbler for transmitting the predetermined compound to the mixing manifold.

7. The computer-implemented olfactory data processing system of claim 6, further comprising a one-way check valve structured for transmitting the predetermined compound to the mixing manifold.

8. The computer-implemented olfactory data processing system of claim 1, wherein the mixing manifold comprises a solenoid valve manifold.

9. The computer-implemented olfactory data processing system of claim 1, further comprising at least one additional MFC configured for diluting or regulating a concentration of the sample.

10. The computer-implemented olfactory data processing system of claim 1, further comprising a source of positive air flow in communication with the at least one MFC.

11. The computer-implemented olfactory data processing system of claim 1, further comprising a concentration sensor configured to measure a gas concentration of the test sample and to communicate feedback concentration data to the system controller.

12. The computer-implemented olfactory data processing system of claim 11, further comprising the system controller programmed for dynamically adjusting at least one flow rate associated with the at least one MFC.

13. The computer-implemented olfactory data processing system of claim 1, further comprising the system controller programmed for automated execution of at least one task based on receiving a configuration file or input data file.

14. The computer-implemented olfactory data processing system of claim 13, wherein the configuration file or the input data file comprises at least one operational parameter and at least one measurement parameter for use by the system controller to assess at least one attribute of the test sample.

15. The computer-implemented olfactory data processing system of claim 14, wherein the at least one operational parameter comprises at least one of relay indicia, compound or vapor data, vial data, a baseline time, a sampling time, a recovery time, and/or an MFC flow rate.

16. The computer-implemented olfactory data processing system of claim 1, further comprising the system controller programmed for enabling machine learning/artificial intelligence model library creation in response to at least a portion of collected sensor data.

17. The computer-implemented olfactory data processing system of claim 1, further comprising the system controller programmed for performing at least one stability study in response to at least a portion of collected sensor data.

18. The computer-implemented olfactory data processing system of claim 1, further comprising the system controller programmed for performing at least one concentration study in response to at least a portion of collected sensor data.

19. The computer-implemented olfactory data processing system of claim 1, further comprising the system controller programmed for controlling tasks independent of a sensor type.

20. The computer-implemented olfactory data processing system of claim 1, wherein the at least one olfactory attribute is associated with a physical, biological, or chemical attribute of the test sample.

* * * * *